(12) United States Patent
Chatterjee et al.

(10) Patent No.: US 8,614,064 B2
(45) Date of Patent: Dec. 24, 2013

(54) METHODS OF DIAGNOSING ATHEROSCLEROSIS BY MEASURING APOCI

(75) Inventors: Subroto Chatterjee, Columbia, MD (US); Peter O. Kwiterovich, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 630 days.

(21) Appl. No.: 10/557,283

(22) PCT Filed: May 24, 2004

(86) PCT No.: PCT/US2004/016419
§ 371 (c)(1),
(2), (4) Date: Nov. 30, 2006

(87) PCT Pub. No.: WO2005/002505
PCT Pub. Date: Jan. 13, 2005

(65) Prior Publication Data
US 2007/0178438 A1    Aug. 2, 2007

Related U.S. Application Data

(60) Provisional application No. 60/473,224, filed on May 23, 2003, provisional application No. 60/539,769, filed on Jan. 28, 2004.

(51) Int. Cl.
*G01N 33/53*    (2006.01)
*C07K 14/775*    (2006.01)

(52) U.S. Cl.
USPC .......................................... 435/7.1; 530/359

(58) Field of Classification Search
None
See application file for complete search history.

(56) References Cited

PUBLICATIONS

Conde-Knappe et al (2002. Journal of Lipid Research 43: 2136-2145.*
Flapan et al, 1994. Bmj. 309: 1129-1134.*
Mezdour et al, 1997. Journal of Biological Chemistry. 272(21): 13570-13575.*
Rosenfeld et al. 2002. Curr Atheroscler Rep. 4(3): 238-242).*
Kolmakova et al (2004. Arterioscler Thromb Vasc Biol. 24: 264-269).*
Steen et al (2007. Atherosclerosis. 191: 82-89).*
Kwitterovich et al (2005. JAMA. 293: 1891-1899).*
van der Ham et al (2009. Atherosclerosis. 203: 355-357).*
Williams et al, 1997. Arteriosclerosis, Thrombosis, and Vascular Biology. 17: 702-706.*
Colhoun et al, 2002. Diabetes. 51: 1949-1956.*
Bjorkegren et al. Postprandial Enrichment of Remnant Lipoproteins with ApoC-I in Healthy Normolipidemic Men with Early Asymptomatic Atherosclerosis. *Arteriosclerosis Thrombosis and Vascular Biology*. Sep. 2002, vol. 22 No. 9, pp. 1470-1474.
Bjorkegren et al. Accumulation of Apolipoprotein C-I-Rich and Cholesterol-Rich VLDL Remnants During Exaggerated Postprandial Triglyceridemia in Normolipidemic Patients with Coronary Artery Disease. *Circulation*, 101: 227-230, 2000.
Karpe et al. Remnant Lipoproteins are Related to Intima-Media Thickness of the Carotid Artery Independently of LDL Cholesterol and Plasma Triglycerides. *Journal of Lipid Research*, Jan. 2001; 42: 17-21.

* cited by examiner

*Primary Examiner* — Zachary Howard
(74) *Attorney, Agent, or Firm* — Edwards Wildman Palmer LLP; Peter F. Corless; Richard B. Emmons

(57) ABSTRACT

The present invention provides methods and compositions for identifying compounds which inhibit ApoCI and which are useful in the treatment or prevention of atherosclerosis, plaque rupture, apoptosis, or myocardial infarction. The invention further provides methods for treating subjects suffering from or at risk of developing atherosclerosis, plaque rupture, apoptosis, or myocardial infarction. The invention further provides methods for diagnosing subjects at suffering from or at risk of developing treatment or prevention of atherosclerosis, plaque rupture, apoptosis, or myocardial infarction.

5 Claims, 16 Drawing Sheets

A

B

METHODS OF DIAGNOSING ATHEROSCLEROSIS BY MEASURING APOCI

RELATED APPLICATIONS

This application is a 371 national stage application of PCT/US04/16419, which claims the benefit of U.S. Provisional Application Ser. No. 60/539,769, filed on Jan. 28, 2004, and U.S. Provisional Application Ser. No. 60/473,224, filed on May 23, 2003. The entire contents of each of these applications is incorporated herein by this reference.

BACKGROUND OF THE INVENTION

1. Field of the Invention

The present invention features methods and compositions for identifying compounds which inhibit ApoCI and which are useful in the treatment or prevention of atherosclerosis, plaque rupture, apoptosis, or myocardial infarction. The invention further features methods for treating subjects suffering from or at risk of developing atherosclerosis, plaque rupture, apoptosis, or myocardial infarction. The invention further features methods for diagnosing subjects at suffering from or at risk of developing treatment or prevention of atherosclerosis, plaque rupture, apoptosis, or myocardial infarction.

2. Background

Over the last decade, considerable body of evidence indicates that premature plaque rupture due to apoptotic death of aortic smooth muscle cells (ASMC) in the fibrous cap is a major contributor to the pathological sequelae of atherosclerosis, i.e. arterial thrombosis (Godfrey K M and Barker D J P (2000) Am. J. Clin. Nutr. 71(Suppl):1344S-352S; Kwiterovich, Jr., P O. et al. (2002) Am. J. Card. 90(Suppl 8A):1i-10i; Kwiterovich Jr P O. et al. (In press, 2004) Ethn. Dis.) leading to myocardial infarctions (Diaz M. et al. (1989) Metabolism. 38:435-8) or stroke (Kaser S. et al. (2001) Metabolism. 50:723-8). Other studies based upon the use of carotid artery biopsies and immunohistochemical techniques reveal that macrophages and T lymphocytes are the major cell type found closely associated with the sites of plaque rupture in human subjects (Diaz M. et al. (1989) Metabolism. 38:435-8). Caspases are cystein-aspartate specific proteases and contribute critically in the final phase of apoptosis i.e. executing the cleavage of DNA, an irreversible process in apoptosis. Both caspase-1 and caspase-3 have been implicated to contribute to the execution phase of apoptosis in vivo in human atherosclerotic plaques (Merzouk H. et al. (1997) Acta. Paediatr. 86:528-32; Radunovic N. et al. (2000) J. Clin. Endocrin. Metab. 85:85-88).

Apolipoprotein C-I (ApoCI), a 6.6-kDa single-chain plasma protein of 57 amino acids, has a basic pI because of its high content of lysine (16 mol %) and contains no histidine, tyrosine, cysteine, or carbohydrate (Jong, M. C. et al. (1999) Arterioscler. Thromb. Vasc. Biol. 19:472-484; Shachter, N. S. (2001) Curr. Opin. Lipidol. 12:297-304). Residues 7 to 24 and 35 to 53 of ApoCI are important for binding to plasma lipids (Jong, M. C. et al. (1999) Arterioscler. Thromb. Vasc. Biol. 19:472-484; Shachter, N. S. (2001) Curr. Opin. Lipidol. 12:297-304). ApoCI is a component of very-low-density (VLDL), intermediate density, and high-density lipoproteins (HDL). ApoCI displaces apolipoprotein E (apoE) from VLDL and intermediate density, thereby decreasing their clearance from plasma (Windler, E. E. and Havel R. J. (1985) J. Lipid Res. 26:556-565). ApoCI decreases the binding of β-VLDL to a remnant receptor, the low-density lipoprotein (LDL) receptor-related protein (LRP) (Kowal R. C. et al. (1990) J. Biol. Chem. 265:10771-10779; Weisgraber, K. H. et al. (1990) J. Biol. Chem. 265:22453-22459), and apoE-mediated binding of VLDL and intermediate density to the LDL receptor (LDLR) (Windler, E. E. et al. (1980) J. Biol. Chem. 255:10464-10471; Sehayek, E. and Eisenberg, S. (1991) J. Biol. Chem. 266:18259-18267). ApoCI inhibits cholesterol ester transfer protein (Gautier, T. et al. (2000) J. Biol. Chem. 275:37504-37509) and phospholipase A2 activity (Poensgen, J. (1990) Biochim. Biophys. Acta 1042:188-192). ApoCI stimulates lecithin cholesterol acyl transferase to ~80% of that of apolipoprotein A-I (apoA-I) (Soutar, A. K. et al. (1975) Biochemistry 14:3057-3064).

Human ApoCI-transgenic mice, with a wild-type background or with a knockout background for the LDLR or apoE, manifest a marked combined hyperlipidemia because of significantly delayed remnant clearance (Shachter, N. S. et al. (1996) J. Clin. Invest. 98:846-855; Jong, M. C. et al. (1998) J. Clin. Invest. 101:145-152; Jong, M. C. et al. (2001) Diabetes 50:2779-2785; Jong, M. C. et al. (1996) J. Clin. Invest. 98:2259-2267; Jong, M. C. et al. (1999) Biochem. J. 338:281-287; Jong, M. C. et al. (1996) Arterioscler. Thromb. Vasc. Biol. 16:934-940; Conde-Knape, K. et al. (2002) J. Lipid Res. 43:2136-2145). Free fatty acid levels are elevated because of reduced fatty acid uptake in peripheral tissues, which is an effect that is paradoxically associated with increased sensitivity to insulin and protection from obesity (Jong, M. C. et al. (1998) J. Clin. Invest. 101:145-152; Jong, M. C. et al. (2001) Diabetes 50:2779-2785). Of particular interest here, Conde-Knape et al (Conde-Knape, K. et al. (2002) J. Lipid Res. 43:2136-2145), using a moderately expressing ApoCI transgenic on apoE-null background to study the effect of ApoCI independent of apoE, found a marked combined dyslipidemia that included an ApoCI-enriched HDL and increased atherosclerosis. ApoCI-enriched HDL (but not VLDL) had a marked inhibitory effect on hepatic lipase (Conde-Knape, K et al. (2002) J. Lipid Res. 43:2136-2145). ApoCI knockouts are normolipidemic rather than hypolipidemic (van Ree, J. H. et al. (1995) Biochem. J. 305:905-911). Cholesterol ester transfer protein-transgenic/apoCI knockout mice manifest a markedly increased transfer of cholesteryl esters from HDL to VLDL (Gautier, T. et al. (2002) J. Biol. Chem. 277:31354-31363).

In humans, Bjorkegren et al reported a significant enrichment of ApoCI in VLDL remnants in normolipidemic patients with coronary artery disease and exaggerated postprandial triglyceridemia (Bjorkegren, J. et al. (2000) Circulation 101:227-230) and in healthy, normolipidemic men with early asymptomatic atherosclerosis (Bjorkegren, J. et al. (2002) Arterioscler Thromb Vasc Biol. 22:1470-1474).

SUMMARY OF THE INVENTION

The present invention is based, at least in part, on the discovery that treatment of aortic smooth muscles cells (ASMC) with ApoCI or ApoCI-enriched HDL particles induces apoptosis that accompanied the activation of the neutral sphingomyelinase signal transduction cascade. Increased plasma levels of ApoCI, perhaps associated with HDL, may contribute to the complications of atherosclerosis by inducing apoptosis in ASMC, a biochemical mechanism that contributes to plaque rupture and coronary artery disease. This invention is further based, at least in part on the discovery that a prominent ApoCI-enriched HDL peak is present in the blood of low-birthweight infants.

Accordingly, in one embodiment, the invention provides methods of determining whether a subject is at risk for developing atherosclerosis-associated plaque rupture or myocardial infarction comprising measuring the level of ApoCI protein in a biological sample from the subject, and comparing the level of ApoCI protein in the biological sample from the subject to the level of ApoCI protein from a control, wherein an increased level of ApoCI protein as compared to the control indicates that the subject is at risk for developing atherosclerosis-associated plaque rupture or myocardial infarction. The subject may or may not have been previously diagnosed with atherosclerosis. In one embodiment, the subject is an infant (e.g., a low-birthweight infant). In a preferred embodiment, the biological sample is selected from blood, serum, and plasma. In one embodiment, the biological sample is taken from an infant's umbilical cord.

In one embodiment, the level of ApoCI protein is detected by a method selected from the group consisting of Western blot, ELISA, RIA, and/or MALDI-TOF. In antother embodiment, the level of ApoCI protein is detected by measuring ApoCI activity. In a preferred embodiment, ApoCI activity is measured by measuring the ability of ApoCI to activate N-SMase activity. In another embodiment, ApoCI activity is measured by determining the ability of ApoCI to induce apoptosis in a cell.

In another embodiment, the invention provides methods of identifying a compound useful for the treatment or prevention of atherosclerosis, plaque rupture, apoptosis, or myocardial infarction comprising contacting ApoCI polypeptide with a test compound, and determining whether the test compound binds to ApoCI, wherein a test compound that binds to ApoCI is identified as a compound useful for the treatment or prevention of atherosclerosis, plaque rupture, apoptosis, or myocardial infarction.

In another embodiment, the invention provides methods of identifying a compound useful for the treatment or prevention of atherosclerosis, plaque rupture, apoptosis, or myocardial infarction comprising contacting ApoCI polypeptide with a test compound, and determining whether the test compound inhibits ApoCI activity, wherein a test compound that inhibits ApoCI activity is identified as a compound useful for the treatment or prevention of atherosclerosis, plaque rupture, apoptosis, or myocardial infarction. In a preferred embodiment, ApoCI activity is measured by measuring the ability of ApoCI to activiate N-SMase activity. In another embodiment, ApoCI activity is measured by measuring the ability of ApoCI to inihibit expression of SR-BI or ABCA1. In still another embodiment, ApoCI activity is measured by measuring the ability of ApoCI to induce apoptosis in a cell. In preferred embodiments, apoptosis may be measured using a DNA-laddering assay, fluorescence microscopy, by measuring cytochrome c relase, by measuring caspase activation (e.g., caspase-3 activation), In a preferred embodiment, the cell is a vascular smooth muscle cell (e.g., an aortic smooth muscle cell).

In another embodiment, the invention provides methods of identifying a compound useful for the treatment or prevention of atherosclerosis, plaque rupture, apoptosis, or myocardial infarction comprising contacting a cell (e.g., a liver cell) that expresses ApoCI with a test compound, and determining whether the test compound inhibits ApoCI expression, wherein a test compound that inhibits ApoCI expression is identified as a compound useful for the treatment or prevention of atherosclerosis, plaque rupture, apoptosis, or myocardial infarction.

In one embodiment, ApoCI expression is measured by measuring the level of ApoCI mRNA (e.g., by Northern blotting, primer extension, nuclease protection, and/or RT-PCR). In another embodiment, ApoCI expression is measured by measuring the level of ApoCI polypeptide (e.g., by Western blotting, ELISA, RIA, and/or MALDI-TOF). In a preferred embodiment, the ApoCI polypeptide is secreted into the culture medium.

In a preferred embodiment, the compounds identified using the methods of the invention increase HDL metabolism.

In still another embodiment, the invention provides methods of treating a subject suffering from or at risk for developeing atherosclerosis, plaque rupture, apoptosis, or myocardial infarction comprising administering to the subject a therapeutically effective amount of an ApoCI inhibitor.

In yet another embodiment, the invention provides methods of increasing HDL metabolism in a subject, comprising administering to the subject a therapeutically effective amount of an ApoCI inhibitor.

Other features and advantages of the invention will be apparent from the following detailed description and claims.

BRIEF DESCRIPTION OF THE DRAWINGS

FIG. 1A: The nucleus of normal cells stains blue and the nucleus of apoptotic cells stains is fragmented white. FIG. 1B: 300 to 500 cells in each sample were counted and the percent of apoptotic cells was plotted. Values are mean±SD; $P<0.01$, *$P<0.001$. FIG. 1C: DNA ladder assay. Confluent cultures of ASMC were incubated with control medium alone, ApoCI (2.5 µg/mL medium), ApoCIII (negative control, 2.5 µg/mL medium), and TNF-α (positive control, 20 ng/mL medium). Genomic DNA was extracted and 10 µg DNA was subjected to agarose gel electrophoresis. The gels were calibrated with commercially available DNA standards. After electrophoresis, the gels were stained with ethidium bromide and then photographed.

FIG. 2A: ASMC ($1\times10^3$) were seeded on sterilized glass cover slips and grown in tissue culture medium with 10% fetal calf serum for 48 hours. Next, fresh serum-free medium, with and without GW4869 (20 µmol/L in DMSO), was added to some dishes. Thirty minutes later, vehicle DMSO, ApoCI (2.5 µg/mL), or C2-ceramide (10 µmol/L) were added to dishes, and the incubation continued for 24 hours. The cells were then fixed with ethanol-acetic acid (3:1 v/v), stained with DAPI reagent, assessed by fluorescent microscopy, and photographed. Top to bottom: control cells; cells incubated with ApoCI± the N-SMase inhibitor, GW4869; and cells incubated with ApoCI GW4869, and C2-ceramide. FIG. 2B: The DAPI-stained ASMC from the four experimental conditions described was analyzed for quantitative apoptosis. Mean (SD) from 4 experiments. *$P<0.05$.

FIG. 4C: The cells were incubated with ApoCI alone (2.5 μmol/L) for 5 minutes or preincubated with GW4869 (20 μmol/L) for 30 minutes. After addition of ApoCI (2.5 μg/mL), incubation was continued for 6 hours, 12 hours, and 24 hours. After incubation, cells were harvested and the levels of ceramide determined using the diacylglycerol kinase assay. The level of phosphate was measured and the data (mean±SD) were expressed as percentage of the total ceramide present in untreated cells (vehicle DMSO). *P<0.05. In a separate experiment (FIG. 4D, right), confluent cells were grown on cover slips and pretreated with serum-free medium for 30 minutes. The cells were then incubated with vehicle DMSO alone (control), ApoCI (2.5 μg/ML), or ApoCI (2.5 μg/mL) plus the N-SMase inhibitor GW4869 (20 μmol/L) for 24 hours. The cells were then washed, treated with a primary anticeramide antibody, washed with phosphate-buffered saline, and treated with a fluorescein isothiocyanate-conjugated anti-mouse IgG (FIG. 4C, lower panel).

FIG. 2A: SNR measurements can detect different stages of the atherosclerotic process in the vessel wall since SNR values for group 2 animals are significantly lower than group 3 (p=0.048) and have a trend for significantly lower SNR (p=0.06) when compared to group 1 animals. FIG. 7B: 3D Black blood Fast Spin Echo MRI vessel wall measurements correlated well with histology in animal groups with plaque rupture (r=0.8).

FIG. 8C shows the inverse correlation between serum cholesterol levels (mg/dL) and vessel wall MRI signal in group 2 and 3 animals (r=0.76).

FIG. 10A-*control* (animal group 1) and FIG. 10B-*ruptured* plaque (group 2).

DETAILED DESCRIPTION OF THE INVENTION

Figure 1:
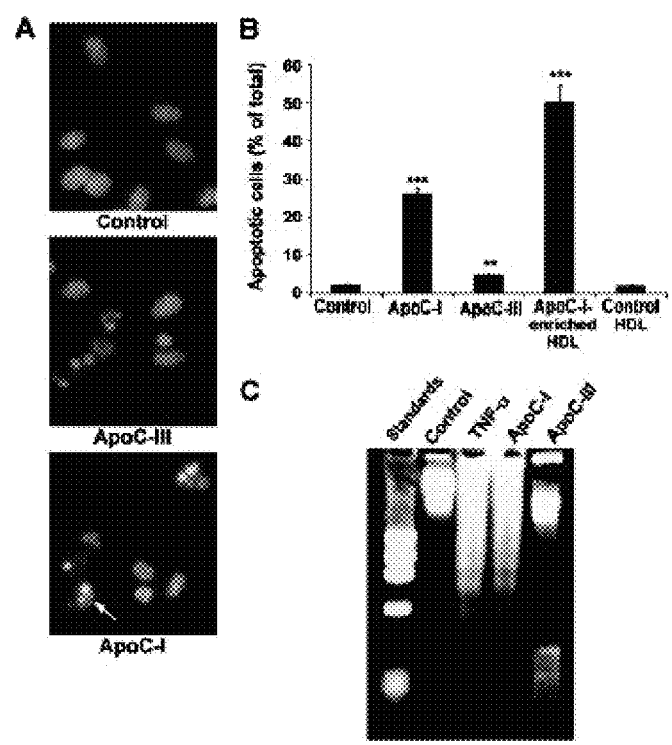
FIGS. 1A-1C depict the effect of apolipoproteins on apoptosis in human aortic smooth muscles cells (ASMC). ASMC were grown on sterilized glass cover slips and incubated for 24 hours with media alone (control), ApoCIII (negative control, 2.5 µg/mL medium), ApoCI (2.5 µg/mL medium), ApoCI-enriched HDL (1 µg apoA-I/mL medium), or ApoCI-poor HDL (5 µg apoA-I/mL medium) for 24 hours. Cells were then fixed with ethanol-acetic acid (3:1 volume/volume) and washed 3 times with phosphate-buffered saline. The cells were then stained with DAPI reagent, mounted on a glass cover slide, and subjected to fluorescence microscopy.

The present invention is based, at least in part, on the discovery that treatment of aortic smooth muscles cells (ASMC) with ApoCI or ApoCI-enriched HDL particles induces apoptosis that accompanied the activation of the neutral sphingomyelinase signal transduction cascade. Increased plasma levels of ApoCI, perhaps associated with HDL, may contribute to the complications of atherosclerosis by inducing apoptosis in ASMC, a biochemical mechanism that contributes to plaque rupture and coronary artery disease. This invention is further based, at least in part on the discovery that a prominent ApoCI-enriched HDL peak is present in the blood of low-birthweight infants. Accordingly, the invention provides methods for identifying subjects at risk for developing plaque rupture and/or myocardial infarction based on measuring the subject's plasma levels of ApoCI. In another embodiment, the invention provides methods for identifying at birth subjects who may later be at risk for atherosclerosis, plaque rupture, and/or myocardial infarction. In still another embodiment, the invention provides methods for identifying compounds which can inhibit ApoCI expression and/or activity.

The data presented herein set for the the initial discovery that human large high density lipoproteins (HDL) enriched in apolipoprotein C-1 (ApoCI), but not control HDL, isolated from umbilical cord blood, induced apoptosis in human cultured arterial smooth muscle cells (ASMC). Highly purified ApoCI, but not ApoCIII, also induced apoptosis in aortic smooth muscle cells (ASMC). This effect was mediated by the activity of neutral sphingomyelinase (N-SMase). ApoCI stimulated Src kinase in addition to N-SMAse, indicating that a second messenger pathway was involved. ApoCI stimulated N-SMase, cleaving sphingomyelin to generate ceramide. In turn, ceramide stimulated the release of cytochrome-C from the mitochondria and contributed to the activation of caspases, resulting in DNA fragmentation and apoptotic cell death of the ASMC. This signal transduction cascade was abrogated by preincuabtion of cells with an antibody against N-SMase. Additional data showed that ApoCI transiently and significantly decreased the cellular level of the scavenger receptor binding protein (SR-BI) and the adenosine triphosphate (ATP) binding cassette (ABC-A1) protein, proteins involved in the cellular uptake of cholesteryl esters from HDL and in the egress of cholesterol from cells onto nascent HDL, respectively. ApoCI did not alter the level of caveolin. Thus, ApoCI also has a role in cellular metabolism of cholesterol via the SRI and ABCA-1 pathways.

ApoCI is a small apolipoprotein secreted from human liver into blood on the triglyceride-rich lipoprotein, very low density lipoprotein (VLDL). ApoCI has several effects in blood. It inhibits the uptake of VLDL by the VLDL receptor, and in transgenic mice promotes hypertriglyceridemia and hypercholesterolemia by decreasing the catabolism and uptake of VLDL. Transgenic ApoCI mice, on a background of LDL receptor deficiency appear to be more propone to atherosclerosis than LDL receptor deficient mice alone but the mechanism of the atherosclerosis is not understood. In addition to its role in VLDL metabolism, ApoCI can be transferred from VLDL up to HDL as a result of lipolysis of triglyceride on VLDL. On HDL, ApoCI can inhibit cholesterol ester transfer protein (CETP), decreasing the transfer of cholesteryl esters from HDL up to VLDL. ApoCI can stimulate lecithin cholesterol ester transferase (LCAT), facilitating the formation of cholesteryl esters on HDL. Thus, ApoCI can also impact HDL metabolism in blood. Despite this literature, the cellular effects of ApoCI, particularly on the cells of the vascular wall, were unknown. As a result of the discoveries detailed herein, ApoCI promotes apoptosis of ASMC. Since ASMC are essential to maintain the integrity of the fibrous cap of the atherosclerotic lesion, apoptosis of the ASCM can promote the rupture of the fibrous cap, leading to heart attack and sudden cardiac death. It provides a cellular mechanism for the promotion of atherosclerosis by ApoCI and the triglyceride-rich lipoproteins. It extends the role of N-SMase in atherosclersois and apoptosis. It also provides for the first time, a regulatory molecule in blood that effects the expression of two cell surface molecules essential in HDL metabolism and reverse cholesterol transport, the SR-BI and ABCA-1 proteins.

The ApoCI modulators identified according to the methods of the invention can be used to inhibit ApoCI expression and/or activity, including inhibition of N-SMase activity and inhibition of apoptosis, and are, therefore, useful in treating or diagnosing atherosclerosis and apotosis-associated disorders, e.g., plaque rupture and myocardial infarction. For example, inhibition of the activity of an ApoCI molecule can cause decreased apoptosis in the vascular smooth muscle cells of a subject Thus, the ApoCI inhibitors used in the methods of the invention can be used to treat disorders characterized by excessive apoptosis.

As used herein, an "apoptosis-associated disorder" includes a disease, disorder, or condition which is associated with abnormal or aberrant apoptosis.

As used interchangeably herein, "ApoCI activity," "biological activity of ApoCI", or "functional activity of ApoCI," includes an activity exerted by an ApoCI protein, polypeptide or nucleic acid molecule on an ApoCI responsive cell or tissue (e.g., a vascular smooth muscle cell) or on an ApoCI protein substrate (e.g., N-SMase), as determined in vivo, or in vitro, according to standard techniques. ApoCI activity can be a direct activity, such as an association with an ApoCI-target molecule. As used herein, a "substrate" or "target molecule" or "binding partner" is a molecule with which an ApoCI protein binds or interacts in nature, such that ApoCI-mediated function, e.g., modulation of apoptosis, is achieved. An ApoCI target molecule can be a non-polypeptide molecule, or a protein or polypeptide (e.g., an ApoCI receptor or an ApoCI effector). Alternatively, an ApoCI activity is an indirect activity, such as a cellular signaling activity mediated by interaction of the ApoCI protein with an ApoCI target molecule. The biological activities of ApoCI are described herein. For example, the ApoCI proteins can have one or more of the following activities: 1) they modulate N-SMase activity; 2) they modulate apoptosis; 3) they modulate expression of ABCA1 and/or SR-B1; 4) they modulate egress of cholesterol from macrophages; 5) they modulate plaque rupture; and 6) they modulate myocardial infarction. In the context of ApoCI-enriched HDL, referred to herein as "dysfunctional HDL", ApoCI stimulates N-Smase activity, promotes apoptosis, downregulates expression of ABCA1 and SR-B1, downregulate egress of cholesterol from macrophages, increase the risk of plaque rupture, and increase the risk of myocardial infarction.

Various aspects of the invention are described in further detail in the following subsections:

I. Screening Assays:

As described herein, ApoCI induces apoptosis of arterial smooth muscle cells through Neutral Sphingomyelinase (N-SMase) stimulation. Accordingly, the invention provides methods (also referred to herein as "screening assays") for identifying inhibitors, i.e., candidate or test compounds or agents (e.g., peptides, peptidomimetics, small molecules, ribozymes, or ApoCI antisense molecules) which bind to ApoCI proteins, have an inhibitory effect on ApoCI expression or ApoCI activity, or an inhibitory effect on the expression or activity of an ApoCI target molecule. Compounds identified using the assays described herein may be useful for treating atherosclerosis associated disorders. Preferably, an ApoCI inhibitor inhibits ApoCI stimulation of N-SMase, decreases apoptosis, and/or prevents rupture of unstable plaques and/or myocardial infarctions. In another embodiment, the screening assays described herein may be used to identify compounds which have a stimulatory effect on ApoCI activity (and thus, which increase apoptosis), which may be useful in the treatment of proliferative disorders (e.g., cancer, polycystic kidney disease).

Candidate/test compounds include, for example, 1) peptides such as soluble peptides, including Ig-tailed fusion peptides and members of random peptide libraries (see, e.g., Lam, K. S. et al. (1991) Nature 354:82-84; Houghten, R. et al. (1991) Nature 354:84-86) and combinatorial chemistry-derived molecular libraries made of D- and/or L-configuration amino acids; 2) phosphopeptides (e.g., members of random and partially degenerate, directed phosphopeptide libraries, see, e.g., Songyang, Z. et al. (1993) Cell 72:767-778); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer Drug Des. 12:145).

Examples of methods for the synthesis of molecular libraries can be found in the art, for example in: DeWitt et al. (1993) Proc. Natl. Acad. Sci. USA 90:6909; Erb et al. (1994) Proc. Natl. Acad. Sci. USA 91:11422; Zuckermann et al. (1994) J. Med. Chem. 37:2678; Cho et al. (1993) Science 261:1303; Carrell et al. (1994) Angew. Chem. Int. Ed. Engl. 33:2059; Carell et al (1994) Angew. Chem. Int. Ed. Engl. 33:2061; and Gallop et al. (1994) J. Med. Chem. 37:1233.

Libraries of compounds may be presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner U.S. Pat. No. '409), plasmids (Cull et al. (1992) Proc. Natl. Acad. Sci. USA 89:1865-1869) or phage (Scott and Smith (1990) Science 249:386-390; Devlin (1990) Science 249:404-406; Cwirla et al. (1990) Proc. Natl. Acad. Sci. 87:6378-6382; Felici (1991) J. Mol. Biol. 222:301-310; Ladner supra).

In one aspect, an assay is a cell-based assay in which a cell is contacted with an ApoCI protein or biologically active portion thereof and with a test compound, and the ability of the test compound to modulate ApoCI activity is determined. In a preferred embodiment, the biologically active portion of the ApoCI protein includes a domain or motif which can modulate N-SMase activity. Determining the ability of the test compound to modulate ApoCI activity can be accomplished by monitoring, for example, N-SMase activity, or by measuring apoptosis in the cell. The cell, for example, can be of mammalian origin, e.g., a vascular smooth muscle cell such as an aortic smooth muscle cell, an endothelial cell, a macrophage, an epithelial cell, a fibroblast, or a T lympocyte In a preferred embodiment N-SMase activity is measured using methods described herein in the Examples section, or using a standard activity gel assay such as the assay disclosed in Example 1, part 6 of U.S. Pat. No. 5,919,687, and includes measuring activity of the N-SMase peptide using [$^{14}$C]-sphingomyelin.

In another embodiment, N-SMase activity is measured by measuring the expression levels of two key cell surface molecules involved in HDL metabolism, ABCA-1 and SR-BI.

The ability of the test compound to modulate ApoCI binding to a target molecule can also be determined. Determining the ability of the test compound to modulate ApoCI binding to a target molecule can be accomplished, for example, by coupling the ApoCI target molecule with a radioisotope, fluorescent, or enzymatic label such that binding of the ApoCI target molecule to ApoCI can be determined by detecting the labeled ApoCI target molecule in a complex. Alternatively, ApoCI could be coupled with a radioisotope or enzymatic label to monitor the ability of a test compound to modulate ApoCI binding to an ApoCI target molecule in a complex. Determining the ability of the test compound to bind ApoCI can be accomplished, for example, by coupling the compound with a radioisotope or enzymatic label such that binding of the compound to ApoCI can be determined by detecting the labeled compound in a complex. For example, test compounds and/or ApoCI target molecules can be labeled with $^{125}$I, $^{35}$S, $^{14}$C, or $^{3}$H, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound to interact with ApoCI without the labeling of any of the interactants. For example, a microphysiometer can be used to detect the interaction of a compound with ApoCI and/or with a ApoCI target molecule without the labeling of any of the interatants (McConnell, H. M. et al. (1992) Science 257:1906-1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and ApoCI.

Because ApoCI modulates N-SMase activity and apoptosis, compounds which modulate N-SMase activity and/or apoptosis can be identified by the ability to modulate ApoCI expression. To determine whether a test compound modulates ApoCI expression, a cell which expresses ApoCI is contacted with a test compound, and the ability of the test compound to modulate ApoCI expression can be determined by measuring ApoCI mRNA by, e.g., Northern blotting, quantitative PCR (e.g., RT-PCR), or in vitro transcriptional assays. To perform an in vitro transcriptional assay, the full length promoter and enhancer of ApoCI can be linked to a reporter gene such as chloramphenicol acetyltransferase (CAT), luciferase, or a fluorescent protein (e.g., GFP and variants thereof) and introduced into host cells. The same host cells can then be transfected with or contacted with the test compound. The effect of the test compound can be measured by reporter gene activity and comparing it to reporter gene activity in cells which do not contain the test compound. An increase or decrease in reporter gene activity indicates a modulation of ApoCI expression and is, therefore, an indicator of the ability of the test compound to modulate apoptosis.

In yet another embodiment, an assay of the present invention is a cell-free assay in which an ApoCI protein or biologically active portion thereof is contacted with a test compound and the ability of the test compound to bind to or to modulate (e.g., inhibit) the activity of the ApoCI protein or biologically active portion thereof is determined. Preferred biologically active portions of the ApoCI proteins to be used in assays of the present invention include fragments which participate in interactions with non-ApoCI molecules. Binding of the test compound to the ApoCI protein can be determined either directly or indirectly as described above. Determining the ability of the ApoCI protein to bind to a test compound can also be accomplished using a technology such as real-time Biomolecular Interaction Analysis (BIA) (Sjolander, S. and Urbaniczky, C. (1991) Anal Chem. 63:2338-2345; Szabo et al. (1995) Curr. Opin. Struct. Biol. 5:699-705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In yet another embodiment, the cell-free assay involves contacting an ApoCI protein or biologically active portion thereof with a known compound which binds the ApoCI protein to form an assay mixture, contacting the assay mixture with a test compound, and determining the ability of the test compound to interact with the ApoCI protein, wherein determining the ability of the test compound to interact with the ApoCI protein comprises determining the ability of the ApoCI protein to preferentially bind to or modulate the activity of an ApoCI target molecule.

The cell-free assays of the present invention are amenable to use of both soluble and/or membrane-bound forms of isolated proteins. In the case of cell-free assays in which a membrane-bound form of an isolated protein is used it may be desirable to utilize a solubilizing agent such that the membrane-bound form of the isolated protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether).sub.n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either ApoCI or an ApoCI target molecule to facilitate separation of complexed from uncomplexed forms of one or both of the proteins, as well as to accommodate automation of the assay. Binding of a test compound to an ApoCI protein, or interaction of an ApoCI protein with an ApoCI target molecule in the presence and absence of a test compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/ApoCI fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or ApoCI protein, and the mixture incubated under conditions conducive to complex formation (e.g., at physiological conditions for salt and pH). Following incubation, the beads or microtitre plate wells are washed to remove any unbound components, the matrix is immobilized in the case of beads, and complex formation is determined either directly or indirectly, for example, as described above. Alternatively, the complexes can be dissociated from the matrix, and the level of ApoCI binding or activity determined using standard techniques. In a preferred embodiment, ApoCI protein or ApoCI target molecule may be immobilized (e.g., for high-throughput screening) in microtiter plates coated with polyvinyldiflouride (PVDF).

Other techniques for immobilizing proteins or cell membrane preparations on matrices can also be used in the screening assays of the invention. For example, either an ApoCI protein or an ApoCI target molecule can be immobilized utilizing conjugation of biotin and streptavidin. Biotinylated ApoCI protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies which are reactive with ApoCI protein or target molecules but which do not interfere with binding of the ApoCI protein to its target molecule can be derivatized to the wells of the plate, and unbound target or ApoCI protein is trapped in the wells by antibody conjugation. Methods for detecting such complexes, in addition to those described above for the GST-immobilized complexes, include immunodetection of complexes using antibodies reactive with the ApoCI protein or target molecule, as well as enzyme-linked assays which rely on detecting an enzymatic activity associated with the ApoCI protein or target molecule.

In yet another aspect of the invention, the ApoCI protein or fragments thereof can be used as "bait proteins" in a two-hybrid assay or three-hybrid assay (see, e.g., U.S. Pat. No. 5,283,317; Zervos et al. (1993) Cell 72:223-232; Madura et al. (1993) J. Biol. Chem. 268:12046-12054; Bartel et al. (1993) Biotechniques 14:920-924; Iwabuchi et al. (1993) Oncogene 8:1693-1696; and Brent WO 94/10300) to identify other proteins which bind to or interact with ApoCI ("ApoCI-binding proteins" or "ApoCI-bp) and are involved in ApoCI activity. Such ApoCI-binding proteins may be ApoCI inhibitors or activators, and are preferably inhibitors.

The two-hybrid system is based on the modular nature of most transcription factors, which consist of separable DNA-binding and activation domains. Briefly, the assay utilizes two different DNA constructs. In one construct, the gene that codes for an ApoCI protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an ApoCI-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the ApoCI protein.

In another aspect, the invention pertains to a combination of two or more of the assays described herein. For example, a modulating agent can be identified using a cell-based or a cell-free assay, and the ability of the agent to modulate the activity of an ApoCI protein can be confirmed in vivo, e.g., in an animal such as an animal model for atherosclerosis.

Moreover, an ApoCI modulator identified as described herein (e.g., an antisense ApoCI nucleic acid molecule, an ApoCI-specific antibody, or a small molecule) can be used in an animal model to determine the efficacy, toxicity, or side effects of treatment with such a modulator. Alternatively, an ApoCI modulator identified as described herein can be used in an animal model to determine the mechanism of action of such a modulator.

II. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining ApoCI protein levels in the context of a biological sample (e.g., blood, serum, or plasma) to thereby determine whether an individual is at risk for atherosclerotic plaque rupture and/or myocardial infarction. Such assays can be used for prognostic or predictive purpose to thereby prophylactically treat an individual prior to the onset of plaque rupture and/or myocardial infarction.

Another aspect of the invention pertains to monitoring the influence of ApoCI inhibitors (e.g., anti-ApoCI antibodies, ribozymes, or small molecules) on the expression or activity of ApoCI in clinical trials.

The present invention further pertains to methods for identifying subjects having or at risk of developing atherosclerosis, plaque rupture, and/or myocardial infarction associated with aberrant ApoCI expression or activity.

As used herein, the term "aberrant" includes an ApoCI expression or activity which deviates from the wild type ApoCI expression or activity. Aberrant expression or activity generally includes increased expression or activity, as well as expression or activity which does not follow the wild type developmental pattern of expression.

In one embodiment, a subject is already known to have atherosclerosis and/or myocardial infarction. In another embodiment, a subject has known risk factors for developing atherosclerosis and/or myocardial infarction (e.g., age, overweight, diabetes, smoking, and/or high-fat diet). In still another preferred embodiment, a subject is a low-birthweight and/or low gestational-age infant. In another embodiment, a subject has been diagnosed as having a ruptured or rupturing plaque using magnetic resonance imaging (MRI)>

To determine whether a subject is at risk for developing plaque rupture and/or myocardial infarction, a biological sample may be obtained from a subject and the biological sample may be contacted with a compound or an agent capable of detecting an ApoCI protein in the biological sample.

A preferred agent for detecting ApoCI protein in a sample is an antibody capable of binding to ApoCI protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically liking) a detectable substance to the probe or antibody, as well as indirect labeling of the probe or antibody by reactivity with another reagent that is directly labeled. Examples of direct substances that can be coupled to an antibody or a nucleic acid probe include various enzymes, prosthetic groups, fluorescent materials, luminescent materials, bioluminescent materials, and radioactive materials. Examples of indirect labeling include detection of a primary antibody using a fluorescently labeled secondary antibody and end-labeling of a DNA probe with biotin such that it can be detected with fluorescently labeled streptavidin.

The term "biological sample" is intended to include tissues, cells, and biological fluids isolated from a subject, as well as tissues, cells, and fluids present within a subject. Preferably, a biological sample is plasma, serum, or blooded. The detection method of the invention can be used to detect ApoCI protein in a biological sample in vitro as well as in vivo. In vitro techniques for detection of ApoCI protein include, but are not limited to, enzyme linked immunosorbent assays (ELISAs), Western blots, immunoprecipitations and immunofluorescence. In vivo techniques for detection of ApoCI protein include introducing into a subject a labeled anti-ApoCI antibody. For example, the antibody can be labeled with a radioactive marker whose presence and location in a subject can be detected by standard imaging techniques.

In another embodiment, the methods further involve obtaining a control biological sample from a control subject, contacting the control sample with a compound or agent capable of detecting ApoCI protein, such that the presence of ApoCI protein is detected in the biological sample, and comparing the presence of ApoCI protein in the control sample with the presence of ApoCI protein in the test sample.

Furthermore, the prognostic assays described herein can be used to determine whether a subject can be administered an ApoCI inhibitor (e.g., an antagonist, peptidomimetic, protein, peptide, nucleic acid, or small molecule) to effectively treat atherosclerosis.

The present invention further provides methods for determining the effectiveness of an ApoCI inhibitor (e.g., an ApoCI inhibitor identified herein) in treating atherosclerosis in a subject. For example, the effectiveness of an ApoCI inhibitor in decreasing ApoCI protein levels, gene expression or activity, can be monitored in clinical trials of subjects exhibiting increased ApoCI gene expression, protein levels, or activity. In such clinical trials, the expression or activity of an ApoCI protein, and preferably, other genes that have been implicated in, for example, atherosclerosis, plaque rupture, and/or myocardial infarction, can be used as a "read out" or marker of the phenotype of a particular cell.

For example, and not by way of limitation, genes, including N-SMase, that are modulated in cells by treatment with an agent which inhibits ApoCI activity (e.g., identified in a screening assay as described herein) can be identified. Thus, to study the effect of agents which modulate ApoCI activity on subjects suffering from a atherosclerosis in, for example, a clinical trial, cells can be isolated and analyzed for the levels of activity or expression of N-SMase and other genes (e.g., caspases) implicated in atherosclerosis (e.g., apoptosis associated genes). The levels of gene expression (e.g., a gene expression pattern) can be quantified by Northern blot analysis or RT-PCR, as described herein, or alternatively by measuring the amount of protein produced, by one of the methods described herein, or by measuring the levels of activity of N-SMase or other genes. In this way, the gene expression or activity pattern can serve as a marker, indicative of the physiological response of the cells to the agent which inhibits ApoCI activity. This response state may be determined before, and at various points during treatment of the individual with the agent which inhibits ApoCI activity.

In a preferred embodiment, the present invention provides a method for monitoring the effectiveness of treatment of a subject with an agent which inhibits ApoCI activity (e.g., an antagonist, peptidomimetic, protein, peptide, nucleic acid, or small molecule identified by the screening assays described herein) including the steps of (i) obtaining a pre-administration sample from a subject prior to administration of the agent; (ii) detecting the level of expression of an ApoCI protein in the pre-administration sample, or the level of N-SMase activity in the pre-administration sample; (iii) obtaining one or more post-administration samples from the subject; (iv) detecting the level of expression or activity of the ApoCI protein in the post-administration samples, or the level of activity of N-SMase in the post-administration sample; (v) comparing the level of expression or activity of the ApoCI protein, or the level of N-SMase in the pre-administration sample with the ApoCI protein, or the level of N-SMase in the post administration sample or samples; and (vi) altering the administration of the agent to the subject accordingly. For example, increased administration of the agent may be desirable to decrease the expression or activity of ApoCI to lower levels than detected, i.e., to increase the effectiveness of the agent. Alternatively, decreased administration of the agent may be desirable, e.g., to decrease side effects. According to such an embodiment, ApoCI expression or activity may be used as an indicator of the effectiveness of an agent, even in the absence of an observable phenotypic response.

III. Methods of Treatment of Subjects Suffering From or at Risk for Atherosclerosis The present invention provides for both prophylactic and therapeutic methods of treating a subject, e.g., a human, at risk of (or susceptible to) developing plaque rupure and/or myocardial infarction. As used herein, "treatment" of a subject includes the application or administration of a therapeutic agent to a subject, or application or administration of a therapeutic agent to a cell or tissue from a subject, who has a diseases or disorders has a symptom of a disease or disorder, or is at risk of (or susceptible to) a disease or disorder, with the purpose to cure, heal, alleviate, relieve, alter, remedy, ameliorate, improve, or affect the disease or disorder, the symptom of the disease or disorder, or the risk of (or susceptibility to) the disease or disorder. As used herein, a "therapeutic agent" includes, but is not limited to, small molecules, peptides, polypeptides, antibodies, ribozymes, and antisense oligonucleotides.

A. Prophylactic Methods

In one aspect, the invention provides a method for preventing in a subject, plaque rupture and/or myocardial infarction by administering to the subject an agent which inhibits ApoCI expression or ApoCI activity, e.g., modulation of N-SMase in cells, e.g., vascular smooth muscle cells. Subjects at risk for plaque rupture and/or myocardial infarction can be identified by, for example, any or a combination of the diagnostic or prognostic assays described herein. Administration of a prophylactic agent can occur prior to the manifestation of symptoms characteristic of aberrant ApoCI expression or activity, such that plaque rupture and/or myocardial infarction (e.g., acute unstable angina pectoris) is prevented or, alternatively, delayed in its progression. Depending on the type of ApoCI aberrancy, for example, an ApoCI antagonist agent can be used for treating the subject. The appropriate agent can be determined based on screening assays described herein.

B. Therapeutic Methods

Another aspect of the invention pertains to methods for treating a subject suffering from atherosclerosis. These methods involve administering to a subject an agent which inhibits ApoCI expression or activity (e.g., an agent identified by a screening assay described herein), or a combination of such agents.

Inhibition of ApoCI activity is desirable in situations in which ApoCI is abnormally upregulated and/or in which decreased ApoCI activity is likely to have a beneficial effect, e.g., a decrease in N-SMase activity.

In another embodiment, the invention pertains to methods for treating a subject suffering from a proliferative disorder, e.g., a disorder in which induction of apoptosis by ApoCI activity may be beneficial, for example, cancer or polycystic kidney disease. Subjects suffering from such a disorder may benefit from adminstration of an ApoCI agonist.

The agents which inhibit ApoCI activity can be administered to a subject using pharmaceutical compositions suitable for such administration. Such compositions typically comprise the agent (e.g., nucleic acid molecule, protein, or antibody) and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition used in the therapeutic methods of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polytheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the agent that inhibits ApoCI activity in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, strawberry, cherry, mango, lemon, lime, raspberry, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The agents that inhibit ApoCI activity can also be prepared in the form of suppositories (e.g., with conventional suppository bases such as cocoa butter and other glycerides) or retention enemas for rectal delivery.

In one embodiment, the agents that inhibit ApoCI activity are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the agent that inhibits ApoCI activity and the particular therapeutic effect to be achieved, and the limitations inherent in the art of compounding such an agent for the treatment of subjects.

In another embodiment, ApoCI antagonist or agonist compounds may be administered by adsorbing the compounds to a biopolymer, e.g., a biopolymer coated-stent, which may be delievered directly to a site in the body, e.g., to a blood vessel containing a plaque (e.g., a rupturing or ruptured plaque).

Toxicity and therapeutic efficacy of such agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and can be expressed as the ratio LD50/ED50. Agents which exhibit large therapeutic indices are preferred. While agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage for use in humans. The dosage of such ApoCI inhibitors lies preferably within a range of circulating concentrations that include the ED50 with little or no toxicity. The dosage may vary within this range depending upon the dosage form employed and the route of administration utilized. For any agent used in the therapeutic methods of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies for Immunotargeting of Drugs in Cancer Therapy", in Monoclonal Antibodies and Cancer Therapy, Reisfeld et al. (eds.), pp. 243-56 (Alan R. Liss, Inc. 1985); Hellstrom et al., "Antibodies for Drug Delivery", in Controlled Drug Delivery (2nd Ed.), Robinson et al. (eds.), pp. 623-53 (Marcel Dekker, Inc. 1987); Thorpe, "Antibody Carriers of Cytotoxic Agents in Cancer Therapy: A Review", in Monoclonal Antibodies '84: Biological and Clinical Applications, Pinchera et al. (eds.), pp. 475-506 (1985); "Analysis, Results, and Future Prospective of the Therapeutic Use of Radiolabeled Antibody in Cancer Therapy", in Monoclonal Antibodies for Cancer Detection and Therapy, Baldwin et al. (eds.), pp. 303-16 (Academic Press 1985), and Thorpe et al. (1982) "The Preparation and Cytotoxic Properties of Antibody-Toxin Conjugates", Immunol. Rev. 62:119-58. Alternatively, an antibody can be conjugated to a second antibody to form an antibody heteroconjugate as described by Segal in U.S. Pat. No. 4,676,980.

The nucleic acid molecules used in the methods of the invention can be inserted into vectors and used as gene therapy vectors. Gene therapy vectors can be delivered to a subject by, for example, intravenous injection, local administration (see U.S. Pat. No. 5,328,470) or by stereotactic injection (see, e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

In a preferred embodiment, an ApoCI inhibitor may be administered to a subject in conduction with any known treatment and/or agent useful for treating atherosclerosis and/or myocardial infarction.

IV. Recombinant Expression Vectors and Host Cells Used in the Methods of the Invention The methods of the invention (e.g., the screening assays described herein) include the use of vectors, preferably expression vectors, containing nucleic acid molecules encoding an ApoCI protein (or a portion thereof), as well as ApoCI target molecules (e.g., N-SMase), or portions thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors to be used in the methods of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel (1990) Methods Enzymol. 185:3-7. Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., ApoCI proteins, ApoCI target molecules, mutant forms of ApoCI proteins and/or ApoCI target molecules, fusion proteins, and the like).

The recombinant expression vectors to be used in the methods of the invention can be designed for expression of ApoCI proteins in prokaryotic or eukaryotic cells. For example, ApoCI proteins can be expressed in bacterial cells such as *E. coli*, insect cells (using baculovirus expression vectors), yeast cells, or mammalian cells. Suitable host cells are discussed further in Goeddel (1990) supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:3140), pMAL (New England Biolabs, Beverly, Mass.) and pRIT5 Pharmacia, Piscataway, N.J.) which fuse glutathione S-transferase (GST), maltose E binding protein, or protein A, respectively, to the target recombinant protein.

Purified fusion proteins can be utilized in ApoCI activity assays (e.g., direct assays or competitive assays described in detail below), or to generate antibodies specific for ApoCI proteins. In a preferred embodiment, an ApoCI fusion protein expressed in a retroviral expression vector of the present invention can be utilized to infect bone marrow cells which are subsequently transplanted into irradiated recipients. The pathology of the subject recipient is then examined after sufficient time has passed (e.g., six weeks).

In another embodiment, a nucleic acid of the invention is expressed in mammalian cells using a mammalian expression vector. Examples of mammalian expression vectors include pCDM8 (Seed, B. (1987) Nature 329:840) and pMT2PC (Kaufman et al. (1987) EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J. et al., Molecular Cloning: A Laboratory Manual. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid).

The methods of the invention may further use a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to ApoCI mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific, or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes, see Weintraub, H. et al., Antisense RNA as a molecular tool for genetic analysis, Reviews—Trends in Genetics, Vol. 1(1) 1986.

Another aspect of the invention pertains to the use of host cells into which an ApoCI or ApoCI target molecule (such as N-SMase) nucleic acid molecule of the invention is introduced, e.g., an ApoCI or ApoCI target molecule nucleic acid molecule within a recombinant expression vector or an ApoCI or ApoCI target molecule nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an ApoCI protein or ApoCI target molecule can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced-into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (Molecular Cloning: A Laboratory Manual. 2.sup.nd. ed., Cold Spring Harbor Laboratory, Cold Spring Harbor Laboratory Press, Cold Spring Harbor, N.Y., 1989), and other laboratory manuals.

A host cell used in the methods of the invention, such as a prokaryotic or eukaryotic host cell in culture, can be used to produce (i.e., express) an ApoCI protein or ApoCI target molecule. Accordingly, the invention further provides methods for producing an ApoCI protein or ApoCI target molecule using the host cells of the invention. In one embodiment, the method comprises culturing the host cell of the invention (into which a recombinant expression vector encoding an ApoCI protein or ApoCI target molecule has been introduced) in a suitable medium such that an ApoCI protein or ApoCI target molecule is produced. In another embodiment, the method further comprises isolating an ApoCI protein or ApoCI target molecule from the medium or the host cell.

V. Isolated Nucleic Acid Molecules Used in the Methods of the Invention

In a preferred embodiment, the ApoCI polypeptide sequence is set forth as TPDVSSALDKLKEFGNTLED-KARELIBRINKQSELSAKMREWFSETFQKVKELKIDS (SEQ ID NO:1). The ApoCI sequence of SEQ ID NO:1 is a mature polypeptide sequence, i.e., a polypeptide sequence in which the signal sequence has been cleaved off. The cDNA sequence of the isolated human ApoCI gene and the predicted amino acid sequence of the human ApoCI polypeptide are also set forth in GenBank Accession Nos. NM_001645 and NP_001636, respectively. The predicted ApoCI polypeptide disclosed in GenBank Accession No. NP_001636 contains the signal sequence (the signal sequence comprises the first 26 amino acid residues of precursor protein). The contents of all of the above-referenced GenBank records are herein incorporated by reference.

The methods of the invention also use isolated nucleic acid molecules that encode ApoCI target molecules, i.e., proteins which ApoCI interacts with and/or modulates the activity and/or expression of. In a preferred embodiment, an ApoCI target molecule is a protein such as ABCA-1 or SR-BI. Nucleic acid and polypeptide sequences for any of these types of transporters are well-known in the art.

The methods of the invention include the use of isolated nucleic acid molecules that encode ApoCI proteins and ApoCI target molecules or biologically active portions thereof, as well as nucleic acid fragments sufficient for use as hybridization probes to identify ApoCI-encoding and ApoCI target molecule-encoding nucleic acid molecules (e.g., ApoCI and ApoCI target molecule mRNA) and fragments for use as PCR primers for the amplification or mutation of ApoCI and ApoCI target molecule nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

A nucleic acid molecule used in the methods of the present invention, e.g., an ApoCI or ApoCI target molecule nucleic acid molecule, or a portion thereof, can be isolated using standard molecular biology techniques and the sequence information provided herein. Using all or portion of the nucleic acid sequence of an ApoCI or ApoCI target molecule nucleic acid molecule as a hybridization probe, an ApoCI or ApoCI target molecule nucleic acid molecules can be isolated using standard hybridization and cloning techniques (e.g., as described in Sambrook, J. et al., Molecular Cloning: A Laboratory Manual. 2nd. ed., Cold Spring Harbor Laboratory, Cold Spring Harbor Laboratory Press, Cold Spring Harbor, N.Y., 1989).

Moreover, a nucleic acid molecule encompassing all or a portion of an ApoCI or ApoCI target molecule nucleic acid molecule can be isolated by the polymerase chain reaction (PCR) using synthetic oligonucleotide primers designed based upon the sequence of an ApoCI or ApoCI target molecule nucleic acid molecule (e.g., the nucleic acid sequence of SEQ ID NO:1).

A nucleic acid used in the methods of the invention can be amplified using cDNA, mRNA or, alternatively, genomic DNA as a template and appropriate oligonucleotide primers according to standard PCR amplification techniques. Furthermore, oligonucleotides corresponding to ApoCI or ApoCI target molecule nucleotide sequences can be prepared by standard synthetic techniques, e.g., using an automated DNA synthesizer.

Moreover, the nucleic acid molecules used in the methods of the invention can comprise only a portion of the nucleic acid sequence of an ApoCI or ApoCI target molecule nucleic acid molecule, for example, a fragment which can be used as a probe or primer or a fragment encoding a portion of a an ApoCI protein or ApoCI target molecule, e.g., a biologically active portion of an ApoCI protein or ApoCI target molecule. The probe/primer typically comprises substantially purified oligonucleotide.

In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which mis-express an ApoCI protein or ApoCI target molecule, such as by measuring a level of an ApoCI-encoding nucleic acid in a sample of cells from a subject e.g., detecting ApoCI or ApoCI target molecule mRNA levels or determining whether a genomic ApoCI or ApoCI target molecule gene has been mutated or deleted.

The methods of the invention further include the use of allelic variants of human ApoCI, e.g., functional and non-functional allelic variants. Functional allelic variants are naturally occurring amino acid sequence variants of the human ApoCI protein that maintain an ApoCI activity. Functional allelic variants will typically contain only conservative substitution of one or more amino acids of SEQ ID NO:1, or substitution, deletion or insertion of non-critical residues in non-critical regions of the protein. Non-functional allelic variants are naturally occurring amino acid sequence variants of the human ApoCI protein that do not have an ApoCI activity. Non-functional allelic variants will typically contain a non-conservative substitution, deletion, or insertion or premature truncation of the amino acid sequence of SEQ ID NO:1, or a substitution, insertion or deletion in critical residues or critical regions of the protein.

The methods of the present invention may further use orthologues of the ApoCI protein. Orthologues of the ApoCI protein are proteins that are isolated from other organisms and possess the same ApoCI activity.

The methods of the present invention further include the use of nucleic acid molecules comprising in which a mutation has been introduced. The mutation may lead to amino acid substitutions at "non-essential" amino acid residues or at "essential" amino acid residues. A "non-essential" amino acid residue is a residue that can be altered from the wild-type sequence of ApoCI (e.g., the sequence of SEQ ID NO:1) without altering the biological activity, whereas an "essential" amino acid residue is required for biological activity. For example, amino acid residues that are conserved among the ApoCI proteins from different organisms are not likely to be amenable to alteration.

Mutations can be introduced into SEQ ID NO:1 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in an ApoCI protein is preferably replaced with another amino acid residue from the same side chain family. Alternatively, in another embodiment, mutations can be introduced randomly along all or part of an ApoCI coding sequence, such as by saturation mutagenesis, and the resultant mutants can be screened for ApoCI biological activity to identify mutants that retain activity. Following mutagenesis of SEQ ID NO:1, the protein can be expressed recombinantly and the activity of the protein can be determined using an assay described herein.

In other embodiments, the oligonucleotide used in the methods of the invention may include other appended groups such as peptides (e.g., for targeting host cell receptors in vivo), or agents facilitating transport across the cell membrane (see, e.g., Letsinger et al. (1989) Proc. Natl. Acad. Sci. USA 86:6553-6556; Lemaitre et al. (1987) Proc. Natl. Acad. Sci. USA 84:648-652; PCT Publication No. WO 88/09810) or the blood-brain barrier (see, e.g., PCT Publication No. WO 89/10134). In addition, oligonucleotides can be modified with hybridization-triggered cleavage agents (See, e.g., Krol et al. (1988) Biotechniques 6:958-976) or intercalating agents (see, e.g., Zon (1988) Pharm. Res. 5:539-549). To this end, the oligonucleotide may be conjugated to another molecule (e.g., a peptide, hybridization triggered cross-linking agent, transport agent, or hybridization-triggered cleavage agent).

VI. Isolated ApoCI Proteins and ApoCI Target Molecules Used in the Methods of the Invention The methods of the invention include the use of isolated ApoCI proteins and ApoCI target molecules, and biologically active portions thereof, as well as polypeptide fragments suitable for use as immunogens to raise anti-ApoCI and anti-ApoCI target molecule antibodies. In one embodiment, native ApoCI and ApoCI target molecule proteins can be isolated from biological sources by an appropriate purification scheme using standard protein purification techniques. In another embodiment, ApoCI proteins and ApoCI target molecules are produced by recombinant DNA techniques. Alternative to recombinant expression, an ApoCI protein or polypeptide or ApoCI target molecule can be synthesized chemically using standard peptide synthesis techniques.

As used herein, a "biologically active portion" of an ApoCI protein includes a fragment of an ApoCI protein having an ApoCI activity. Biologically active portions of an ApoCI protein include peptides comprising amino acid sequences sufficiently identical to or derived from the amino acid sequence of the ApoCI protein, e.g., the amino acid sequence shown in SEQ ID NO:1, which include fewer amino acids than the full length ApoCI proteins, and exhibit at least one activity of an ApoCI protein. Typically, biologically active portions comprise a domain or motif with at least one activity of the ApoCI protein. A biologically active portion of an ApoCI protein can be a polypeptide which is, for example, 5, 8, 10, 15, 20, 25, 30, 35, 40, 45, 50, 55, 60, 65, 70, 75, 80, or more amino acids in length. Biologically active portions of an ApoCI protein or ApoCI target molecule can be used as targets for developing agents which modulate an ApoCI activity.

In a preferred embodiment, the ApoCI protein used in the methods of the invention has an amino acid sequence shown in SEQ ID NO:1. In other embodiments, the ApoCI protein is substantially identical to SEQ ID NO:1, and retains the functional activity of the protein of SEQ ID NO:1, yet differs in amino acid sequence due to natural allelic variation or mutagenesis, as described in detail in subsection V above. Accordingly, in another embodiment, the ApoCI protein used in the methods of the invention is a protein which comprises an amino acid sequence at least about 50%, 55%, 60%, 65%, 70%, 75%, 80%, 85%, 90%, 95%, 96%, 97%, 98%, 99%, 99.1%, 99.2%, 99.3%, 99.4%, 99.5%, 99.6%, 99.7%, 99.8%, 99.9% or more identical to SEQ ID NO:1.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to an amino acid sequence of having 100 amino acid residues, at least 30, preferably at least 40, more preferably at least 50, even more preferably at least 60, and even more preferably at least 70, 80, 90 or more amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (J. Mol. Biol. 48:444453 (1970)) algorithm which has been incorporated into the GAP program in the GCG software package (available online through the Genetics Computer Group), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online through the Genetics Computer Group), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of Meyers, E. and Miller, W. (Comput. Appl. Biosci. 4:11-17 (1988)) which has been incorporated into the ALIGN program (version 2.0 or 2.0 U), using a PAM120 weight residue table, a gap length penalty of 12 and a gap penalty of 4.

The methods of the invention may also use ApoCI and ApoCI target molecule chimeric or fusion proteins. As used herein, an ApoCI "chimeric protein" or "fusion protein" comprises an ApoCI polypeptide operatively linked to a non-ApoCI polypeptide. A "ApoCI polypeptide" refers to a polypeptide having an amino acid sequence corresponding to an ApoCI molecule, whereas a "non-ApoCI polypeptide" refers to a polypeptide having an amino acid sequence corresponding to a protein which is not substantially homologous to the ApoCI protein, e.g., a protein which is different from the ApoCI protein and which is derived from the same or a different organism. Within an ApoCI fusion protein the ApoCI polypeptide can correspond to all or a portion of an ApoCI protein. In a preferred embodiment, an ApoCI fusion protein comprises at least one biologically active portion of an ApoCI protein. In another preferred embodiment, an ApoCI fusion protein comprises at least two biologically active portions of an ApoCI protein. Within the fusion protein, the term "operatively linked" is intended to indicate that the ApoCI polypeptide and the non-ApoCI polypeptide are fused in-frame to each other. The non-ApoCI polypeptide can be fused to the N-terminus or C-terminus of the ApoCI polypeptide.

For example, in one embodiment, the fusion protein is a GST-ApoCI fusion protein in which the ApoCI sequences are fused to the C-terminus of the GST sequences. Such fusion proteins can facilitate the purification of recombinant ApoCI.

In another embodiment, this fusion protein is a protein containing a heterologous signal sequence at its N-terminus. In certain host cells (e.g., mammalian host cells), expression and/or secretion of a protein can be increased through use of a heterologous signal sequence.

Moreover, the ApoCI-fusion proteins used in the methods of the invention can be used as immunogens to produce anti-ApoCI antibodies in a subject, to purify ApoCI ligands and in screening assays to identify molecules which inhibit the interaction of ApoCI with an ApoCI target molecule.

Preferably, a chimeric or fusion protein used in the methods of the invention is produced by standard recombinant DNA techniques. For example, DNA fragments coding for the different polypeptide' sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al., John Wiley & Sons: 1992). Moreover, many expression vectors are commercially available that already encode a fusion moiety (e.g., a GST polypeptide). An ApoCI or ApoCI target molecule-encoding nucleic acid can be cloned into such an expression vector such that the fusion moiety is linked in-frame to the ApoCI protein or ApoCI target molecule.

The present invention also pertains to the use of variants of the ApoCI proteins or ApoCI target molecules which function as ApoCI antagonists. Variants of the ApoCI proteins or ApoCI target molecules can be generated by mutagenesis, e.g., discrete point mutation or truncation of an ApoCI protein or ApoCI target molecule. An agonist of the ApoCI proteins or ApoCI target molecules can retain substantially the same, or a subset, of the biological activities of the naturally occurring form of the protein. An antagonist of a protein can inhibit one or more of the activities of the naturally occurring form of the protein by, for example, competitively modulating an ApoCI-mediated activity of an ApoCI protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring forms of the ApoCI protein or ApoCI target molecules.

In one embodiment, variants of an ApoCI protein which function as ApoCI antagonists can be identified by screening combinatorial libraries of mutants, e.g., truncation mutants, of an ApoCI protein for ApoCI protein antagonist activity. In one embodiment, a variegated library of ApoCI variants is generated by combinatorial mutagenesis at the nucleic acid level and is encoded by a variegated gene library. A variegated library of ApoCI variants can be produced by, for example, enzymatically ligating a mixture of synthetic oligonucleotides into gene sequences such that a degenerate set of potential ApoCI sequences is expressible as individual polypeptides, or alternatively, as a set of larger fusion proteins (e.g., for phage display) containing the set of ApoCI sequences therein. There are a variety of methods which can be used to produce libraries of potential ApoCI variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential ApoCI sequences. Methods for synthesizing degenerate oligonucleotides are known in the art (see, e.g., Narang, S. A. (1983) Tetrahedron 39:3; Itakura et al. (1984) Annu. Rev. Biochem. 53:323; Itakura et al. (1984) Science 198:1056; Ike et al. (1983) Nucleic Acids Res. 11:477).

In addition, libraries of fragments of an ApoCI protein coding sequence can be used to generate a variegated population of ApoCI fragments for screening and subsequent selection of variants of an ApoCI protein. In one embodiment, a library of coding sequence fragments can be generated by treating a double stranded PCR fragment of an ApoCI coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the ApoCI protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of ApoCI proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify ApoCI variants (Arkin and Youvan (1992) Proc. Natl. Acad. Sci. USA 89:7811-7815; Delagrave et al. (1993) Prot. Eng. 6(3):327-331).

The methods of the present invention further include the use of anti-ApoCI antibodies and anti-ApoCI target molecule antibodies. An isolated ApoCI protein or target molecule, or a portion or fragment thereof, can be used as an immunogen to generate antibodies that bind ApoCI using standard techniques for polyclonal and monoclonal antibody preparation. A full-length protein can be used or, alternatively, antigenic peptide fragments of the protein can be used as immunogens. The antigenic peptide of ApoCI comprises at least 8 amino acid residues of the amino acid sequence shown in SEQ ID NO:1 and encompasses an epitope of ApoCI such that an antibody raised against the peptide forms a specific immune complex with the ApoCI protein. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of ApoCI that are located on the surface of the protein, e.g., hydrophilic regions, as well as regions with high antigenicity.

An ApoCI immunogen is typically used to prepare antibodies by immunizing a suitable subject (e.g., rabbit, goat, mouse, or other mammal) with the immunogen. An appropriate immunogenic preparation can contain, for example, recombinantly expressed ApoCI protein or a chemically synthesized ApoCI polypeptide. The preparation can further include an adjuvant, such as Freund's complete or incomplete adjuvant, or similar immunostimulatory agent. Immunization of a suitable subject with an immunogenic ApoCI preparation induces a polyclonal anti-ApoCI antibody response.

The term "antibody" as used herein refers to immunoglobulin molecules and immunologically active portions of immunoglobulin molecules, i.e., molecules that contain an antigen binding site which specifically binds (immunoreacts with) an antigen, such as an ApoCI. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind ApoCI molecules. The term "monoclonal antibody" or "monoclonal antibody composition", as used herein, refers to a population of antibody molecules that contain only one species of an antigen binding site capable of immunoreacting with a particular epitope of ApoCI. A monoclonal antibody composition thus typically displays a single binding affinity for a particular ApoCI protein with which it immunoreacts.

Polyclonal anti-ApoCI antibodies can be prepared as described above by immunizing a suitable subject with an ApoCI immunogen. The anti-ApoCI antibody titer in the immunized subject can be monitored over time by standard techniques, such as with an enzyme linked immunosorbent assay (ELISA) using immobilized ApoCI. If desired, the antibody molecules directed against ApoCI can be isolated from the mammal (e.g., from the blood) and further purified by well known techniques, such as protein A chromatography to obtain the IgG fraction. At an appropriate time after immunization, e.g., when the anti-ApoCI antibody titers are highest, antibody-producing cells can be obtained from the subject and used to prepare monoclonal antibodies by standard techniques, such as the hybridoma technique originally described by Kohler and Milstein (1975) Nature 256:495-497) (see also, Brown et al. (1981) J. Immunol. 127:539-46; Brown et al. (1980) J. Biol. Chem. 255:4980-83; Yeh et al. (1976) Proc. Natl. Acad. Sci. USA 76:2927-31; and Yeh et al. (1982) Int. J. Cancer 29:269-75), the more recent human B cell hybridoma technique (Kozbor et al. (1983) Immunol. Today 4:72), the EBV-hybridoma technique (Cole et al. (1985) Monoclonal Antibodies and Cancer Therapy, Alan R. Liss, Inc., pp. 77-96) or trioma techniques. The technology for producing monoclonal antibody hybridomas is well known (see generally Kenneth, R. H. in Monoclonal Antibodies: A New Dimension in Biological Analyses, Plenum Publishing Corp., New York, N.Y. (1980); Lerner, E. A. (1981) Yale J. Biol. Med. 54:387-402; Gefter, M. L. et al. (1977) Somat. Cell Genet. 3:231-36). Briefly, an immortal cell line (typically a myeloma) is fused to lymphocytes (typically splenocytes) from a mammal immunized with an ApoCI immunogen as described above, and the culture supernatants of the resulting hybridoma cells are screened to identify a hybridoma producing a monoclonal antibody that binds ApoCI.

Any of the many well known protocols used for fusing lymphocytes and immortalized cell lines can be applied for the purpose of generating an anti-ApoCI monoclonal antibody (see, e.g., Galfre, G. et al. (1977) Nature 266:55052; Gefter et al. (1977) supra; Lerner (1981) supra; and Kenneth (1980) supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind ApoCI, e.g., using a standard ELISA assay.

Alternative to preparing monoclonal antibody-secreting hybridomas, a monoclonal anti-ApoCI antibody can be identified and isolated by screening a recombinant combinatorial immunoglobulin library (e.g., an antibody phage display library) with ApoCI to thereby isolate immunoglobulin library members that bind ApoCI. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, Ladner et al., U.S. Pat. No. 5,223,409; Kang et al., PCT International Publication No. WO 92/18619; Dower et al., PCT International Publication No. WO 91/17271; Winter et al., PCT International Publication No. WO 92/20791; Markland et al., PCT International Publication No. WO 92/15679; Breitling et al., PCT International Publication No. WO 93/01288; McCafferty et al, PCT International Publication No. WO 92/01047; Garrard et al., PCT International Publication No. WO 92/09690; Ladner et al., PCT International Publication No. WO 90/02809; Fuchs et al. (1991) Biotechnology (NY) 9:1369-1372; Hay et al. (1992) Hum. Antibod. Hybridomas 3:81-85; Huse et al. (1989) Science 246:1275-1281; Griffiths et al. (1993) EMBO J. 12:725-734; Hawkins et al. (1992) J. Mol. Biol. 226:889-896; Clackson et al. (1991) Nature 352:624-628; Gram et al. (1992) Proc. Natl. Acad. Sci. USA 89:3576-3580; Garrard et al. (1991) Biotechnology (NY) 9:1373-1377; Hoogenboom et al. (1991) Nucleic Acids Res. 19:4133-4137; Barbas et al. (1991) Proc. Natl. Acad. Sci. USA 88:7978-7982; and McCafferty et al. (1990) Nature 348:552-554.

Additionally, recombinant anti-ApoCI antibodies, such as chimeric and humanized monoclonal antibodies, comprising both human and non-human portions, which can be made using standard recombinant DNA techniques, are within the scope of the methods of the invention. Such chimeric and humanized monoclonal antibodies can be produced by recombinant DNA techniques known in the art, for example using methods described in Robinson et al., International Application No. PCT/US86/02269; Akira et al., European Patent Application No. 184,187; Taniguchi, M., European Patent Application No. 171,496; Morrison et al., European Patent Application No. 173,494; Neuberger et al., PCT International Publication No. WO 86/01533; Cabilly et al., U.S. Pat. No. 4,816,567; Cabilly et al., European Patent Application No. 125,023; Better et al. (1988) Science 240:1041-1043; Liu et al. (1987) Proc. Natl. Acad. Sci. USA 84:3439-3443; Liu et al. (1987) J. Immunol. 139:3521-3526; Sun et al. (1987) Proc. Natl. Acad. Sci. USA 84:214-218; Nishimura et al. (1987) Cancer Res. 47:999-1005; Wood et al. (1985) Nature 314:446-449; Shaw et al. (1988) J. Natl. Cancer Inst. 80:1553-1559; Morrison, S. L. (1985) Science 229:1202-1207; Oi et al. (1986) BioTechniques 4:214; Winter U.S. Pat. No. 5,225,539; Jones et al. (1986) Nature 321:552-525; Verhoeyen et al (1988) Science 239:1534; and Beidler et al. (1988) J. Immunol. 141:4053-4060.

An anti-ApoCI antibody can be used to detect ApoCI protein (e.g., in a biololgical sample, cellular lysate or cell supernatant) in order to evaluate the abundance and pattern of expression of the ApoCI protein. Anti-ApoCI antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, .beta.-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include 125I, 131I, 35S or 3H.

This invention is further illustrated by the following examples which should not be construed as limiting. The contents of all references, patents and published patent applications cited throughout this application, as well as the sequence listing and the figures, are incorporated herein by reference.

EXAMPLES

Materials and Methods

The following materials and methods were used in Examples 1-7.

Isolation of Human ApoCI-Enriched HDL and ApoCI Poor HDL

Two plasma pools (A and B) were prepared from umbilical cord blood. Pool A and pool B consisted of plasma from normal infants with increased or decreased amounts of large HDL particles, respectively. The concentration of ApoCI in pool A was 7.2 mg/dL, and was 3.9 mg/dL in pool B. The ApoB-containing lipoproteins (VLDL, IDL, LDL, and Lp (a)) were then precipitated with heparin manganese (Warnick, G. R., and Albers J J. (1978) J. Lipid Res. 19, 65-76). No ApoB was detected in the heparin manganese supernatant (HMS). All of the ApoCI remained with the HDL in the HMS. The supernatants were then dialyzed against the running buffer (0.5 M Tris HCl, pH 7.4 containing 0.1-5 M NaCl, and 1.5 mg/ml EDTA), and aliquots applied to an antiapoA-II immunosorber. The preparation of the anti-apoA-II immunosorber and the fractionation of the Lp-A-I and Lp-AI:A-II particles have been previously described (Bekaert, E. D., Alaupovic, P., Knight-Gibson, C., Blackett, P., Ayrault-Jarrier, M. (1991). Pediatr. Res. 29, 315-321).

Briefly, the HMS was applied to the antiA-II immunosorber and incubated overnight. The unretained plasma proteins' and the Lp-A-I particles were eluted with the running buffer. The retained Lp-A-I:A-II were eluted with running buffer. The sodium thiocyanate was removed as described (Bekaert, E. D., Alaupovic, P., Knight-Gibson, C., Blackett, P., Ayrault-Jarrier, M. (1991). Pediatr. Res. 29, 315-321), and the concentrated retained fraction consisting of Lp-A-I:A-II particles was applied in the running buffer to an anti-ApoCI-immunosorber, which was prepared with affinity purified ApoCI antibodies according to the procedure used for the preparation of the antiA-II immunosorber. The ApoA-II retained-ApoCI unretained fraction was eluted with the running buffer and the apoA-II retained, ApoCI retained fraction was eluted with 4.5 M sodium thiocyanate, the thiocyanate removed, and the eluate dialyzed against the starting buffer. The apoA-II retained, ApoCI retained particles from pool A, and the apoA-II retained, ApoCI unretained particles from pool B constituted the ApoCI-enriched HDL and the ApoCI-poor HDL, respectively (Table 1). Aliquots of both fractions were taken for determining the lipid and apolipoprotein composition (see also below) (Table 1).

TABLE I

Lipid and Apolipoprotein Composition of ApoCI-enriched HDL, ApoCI-poor HDL and ApoCI-enriched HMS.

|  | ApoCI-enriched HDL | ApoCI-poor HDL | ApoCI-enriched Heparin-Mn ++ Supernatant |
|---|---|---|---|
| Lipids (%) |  |  |  |
| Cholesteryl Esters | 9.8 | 16.2 | 16.3 |
| Free Cholesterol | 1.8 | 2.2 | 3.9 |
| Triglycerides | 2.6 | 1.7 | 0.9 |
| Phospholipids | 33.4 | 30.4 | 37.5 |
| Total Apolipoproteins | 52.2 | 49.5 | 41A |
|  | 100.0 | 100.0 | 100.0 |

TABLE I-continued

Lipid and Apolipoprotein Composition of ApoCI-enriched HDL, ApoCI-poor HDL and ApoCI-enriched HMS.

|  | ApoCI-enriched HDL | ApoCI-poor HDL | ApoCI-enriched Heparin-Mn ++ Supernatant |
|---|---|---|---|
| Apolipoproteins (%) |  |  |  |
| Apo AI | 47.3 | 74.3 | 55.5 |
| Apo AII | 10.2 | 19.1 | 19.6 |
| Apo CI | 6.4 | ND | 5.9 |
| Apo CII | 4.2 | ND | 2.2 |
| Apo CIII | 14.0 | 0.3 | 3.5 |
| Apo D | 8.2 | 3.2 | 3.9 |
| Apo E | 9.5 | 3.0 | 7.5 |
|  | 100.0 | 100.0 | 100.0 |

ApoCI-enriched HDL and ApoCI-poor HDL were isolated from the heparin manganese supernatants of human plasma from umbilical cord blood by immunoaffinity chromatography as described in Methods. ApoCI-enriched HDL is the apoA-II-retained, ApoCI-retained fraction of LpA-I:A-II particles. ApoC-poor HDL is the apoA-II-retained, ApoCI-unretained fraction of LpAI:A-II particles.

These two fractions were then stored frozen at −80° C. until used for cell experiments. The fractions were thawed at that time, dialyzed against the culture medium (see below) and aliquots added to the cell culture dishes.

ApoCI-Enriched Heparin Manganese Supernatant

In several cell experiments, ApoCI-enriched HMS was used. This fraction was prepared from a separate plasma pool from normal infants with increased large HDL. After the apoB-containing lipoproteins were precipitated with heparin manganese (Warnick, G. R., and Albers J J. (1978) J. Lipid Res. 19, 65-76), the supernatant was dialyzed against 0.5 M Tris HCl, pH 7.4 containing 0.15 M NaCl, and 1.5 mg/ml EDTA Aliquots were taken for determining the lipid and apolipoprotein composition (see also below) (Table 1). No apoB was detected in the supernatant. The supernatant was frozen at −80° C. until used for cell experiments. The supernatant was thawed at that time, dialyzed against the culture medium (see below) and aliquots added to the cell culture dishes.

Lipid and Apolipoprotein Composition

Neutral lipids (cholesteryl esters, free cholesterol and triglycerides) were determined by gas chromatography in ApoCI-enriched HDL, ApoCI-poor HDL and HMS by a modified procedure (Lee, D. M. (1999) Atherosclerosis 146, 221-235) of the method of Kuksis et al (Kuksis, A., Myher, J. J., Marai, L., Geher, K. (1975) J. Chromatogr. Sci. 13, 423-430). Phospholipids were measured by the method of Gerlach and Deuticke (Gerlach, E., Deuticke, B. (1963) Biochem. Z. 337, 477-479). The quantitative determination of apolipoproteins was performed by electroimmunoassay for apolipoprotein A-I and apolipoprotein A-II (Curry, M., Alaupovic, P., Suenram, C. A. (1976) Clin. Chem. 22, 315-322), apolipoprotein B (Curry, M. D., Gustafson, A., Alaupovic, P., McConathy, W. J. (1978) Clin. Chem. 24, 280-286), ApoCI and apolipoprotein C-II (Curry, M. D., McConathy, W. J., Fesmire, J. D., Alaupovic, P. (1981) Clin. Chem. 27, 543-548), ApoCI (Curry, M. D., McConathy, W. J., Fesmire, J. D., Alaupovic, P. (1980) Biochim. Biophys. Acta. 617, 503-513), apolipoprotein D (Curry, M. D., McConathy, W. J., Alaupovic, P. (1977) Biochim. Biophys. Acta. 491, 232-241), and apolipoprotein E (Curry, M. D., McConathy, W. J., Alaupovic, P., Ledford, J. H., Popovic, M. (1976) Biochim. Biophys. Acta. 439, 413-425).

Cultured Cells

Human AoSMC that were negative for mycoplasma, hepatitis B and C and HIV-1 were purchased from Clonetics (San Diego, Calif.) and cultured in Dulbecco's minimal essential medium (Invitrogen, Carlsbad, Calif.) with 10% fetal bovine serum (Hyclone, Salt Lake City, Utah), 100-units/ml penicillin, 100-μg/ml streptomycin to confluence. The cells were incubated in serum-free medium for 30 min prior to initiating the experiments. Cells were then washed and harvested in PBS, and centrifuged at 1500 rpm for 5 min at 4° C. Protease inhibitors were then added and the pellets stored frozen at −30° C. until use.

Purified Human ApoCI and ApoCIII

Human ApoCI and ApoCIII were purchased from Academy Bio-Medical Company (Houston, Tex.) and were >99% homogenous by SDS gel-electrophoresis and were lipopolysaccharide-free.

Assessment of Apoptosis

Fluorescence Microscope-Quantitative Assay of Apoptotic Death $1 \times 10^3$ cells were grown on sterilized glass cover slips in 6-well trays and treated with ApoCI (2.5 μg/ml medium), ApoCIII (2.5 μg/ml medium), tumor necrosis factor (TNF)-α (30 ng/ml), ApoCI-enriched HDL (1 μg apoA-I/ml medium) and ApoCI-poor HDL (5 μg apoA-I/ml medium). After 24 h incubation, the medium was removed, cells fixed with ethanol:acetic acid 70:30 (v/v) and stored at 4° C. Next, the fixing solution was removed and cells stored frozen at −30° C. Cover slips were mounted on the microscope slides and stained with DAPI reagent (4,6-diamino-2-phenylindol, dihydrochloride). The stained nuclei were visualized by fluorescence microscopy (Zeiss Axiovert 25). Apoptotic cells were determined after counting—500 cells in a double blind fashion.

DNA Laddering Assay

Cells were treated with either TNF-α (30 ng/ml), ApoCI or ApoCIII (2.5 μg/ml) for 6 h. The cells were then washed twice with minimal essential medium and harvested with buffer (10 mM HEPES, pH 7.4. 5 mM EDTA, 0.25 mM EGTA, 50 mM NaF, 5 mM β-mercaptoethanol, 0.35 M sucrose, 0.1% Nonidet and protease inhibitors, 1 mM phenylmethylsulfonyl fluoride, 2 μg/ml leupeptin and 5 μg/ml pepstatin), and pelleted. Genomic DNA was prepared employing standard protocol. Genomic DNA was subjected to electrophoresis, stained with ethidium bromide and the gel was photographed. The gel was calibrated using DNA fragments of known molecular weight.

Neutral Sphingomyelinase Assay

After stimulation with ApoCI ApoCI-enriched HDL and ApoCI-poor HDL, the cells were washed with 5 ml of PBS and harvested. The pellets were stored frozen at −70° C. and resuspended in 0.5 ml of buffer (100 mM Tris-HCl pH 7.4, 0.1% Triton X-100, 1 mM EDTA and protease inhibitors). The cell suspension was sonicated 3 times (3-s bursts) using a probe sonicator and centrifuged at 500×g at 4° C. for 5 min. The supernatant was used as the enzyme source. 100 μg of protein was assayed for neutral sphingomyelinase activity in a buffer consisting of 50 mM Tris-HCl, pH 7.4, 0.1% Triton X-100, 0.1 mg of bovine serum albumin, 5 mM MgCl$_2$ and 50 μmol of [$^{14}$C]sphingomyelin (specific activity 50 mCi/mmol, from American Radiolabled Chemicals (St. Louis, Mo.). The samples were incubated at 37° C. for 2 h and terminated with the addition of 1 ml of 10% trichloroacetic acid. The precipitate was pelleted (1000×g at 4° C. for 30 min) and 1 ml of the supernatant was extracted with 1 ml of anhydrous diethyl ether. About 0.5 ml of the aqueous phase was removed for liquid scintillation counting (Ghosh, N., and Chatterjee, S. (1998) J. Biol. Chem. 264, 12554-12561).

Measurement of the Ceramide Level

Cells were pelleted and extracted with chloroform-methanol-acetic acid 100:100:2 (v/v/v). Lipids in organic phase were dried in N$_2$ atmosphere and re-extracted, and the organic phase was dried. Detergent solution (30 μl of 7.5%/n-octyl-β-glucopyranoside with 5 mM cardiolipin in 1 mM diethylenimine-pentaacetic acid) was added, and the samples were sonicated. Total inorganic phosphate level was measured employing the method of Bartlett et al. Bartlett, G R. (1959). J. Biol. Chem. 234, 449-458). Ceramide was measured using the sn-1, 2-diacylglycerolkinase-assay reagent system and labeling for 30 min with 1 mCi of [$^{32}$P] ATP in 10 μl of 5 mM ATP (Signorelli, P., and Hannun, Y. A. (2002) Meth. Enzymol. 345, 275-294). Diacylglycerol kinase was from *Streptomyces* species (Calbiochem, San Diego, Calif.). [$^{32}$P] ATP (specific activity 3000 Ci/mmol) was from New England Nuclear Company (Boston, Mass.). Ceramide-1-phosphate and diacylglycerol-1-phosphate were resolved by thin-layer chromatography on silica gel plates (Whatman, Clinton, N.J.), using a solvent composed of chloroform-acetone-methanol-acetic acid-water 10:4:3:2:1(v/v) and detected by autoradiography using an Instant Imager (Packard Canberra Company). Ceramide was expressed as pmol ceramide/nmol phosphate.

Measurements of Cytochrome c Release and Caspase Activation—Mitochondrial and Cytosolic Protein Isolation After incubation with ApoCI (2.5 μg/ml medium), ApoCIII (2.5 μg/ml medium), apoC-1-enriched HDL (1 μg apoA-I/ml medium), or ApoCI-poor HDL (5 μg ApoA-I/ml medium) for 24 h and 48 h, the cells were subjected to extraction with a buffer (30 mM HEPES, pH 7.5, 10 mM KCl, 1.5 mM MgCl$_2$, 5 mM DTI, 2 mM phenylmethylsulfonyl fluoride (PMSF), 1% Nonidet P-40, 0.5% sodium deoxycholate, 0.1% SDS, 2 μg/ml leupeptin, 2 μg/ml aprotinin, 0.5 μg/ml benzamidine, and 250 mM sucrose) on ice for 30 min. Next, the samples were centrifuged at 10,000×g at 4° C. The supernatant was utilized as a source of cytochrome c in Western immunoblot assay. The pellets were lysed in RIPA buffer (phosphate buffer saline, 1% Nonidet P-40, 0.5% sodium deoxycholate, 0.1% SDS, and cocktail of inhibitors described above). The samples were passed through a 21-gauge needle to shear the DNA. Next, 10 μl of PMSF (10 mg/ml) was added and incubation continued for 60 min on ice. The samples were centrifuged at 10,000-×g for 10 min at 4° C. The supernatants were used as a source of protein in Western immunoblot assay for determination of caspase activation. Proteins (100 μg) were separated using 4-15% SDS-polyacrylamide gel under denaturing conditions and electro transferred onto nitrocellulose. Membranes were then incubated with primary antibody (anti cytochrome c and anti caspase-3 rabbit polyclonal antibody (1:300) (Santa Cruz Biotechnology, Santa Cruz, Calif.) and horseradish labeled anti-rabbit antibody (1:3000).

Immunofluorescence of Cytochrome c in Human Cultured Aortic Smooth Muscle Cells

AOSMC ($5 \times 10^3$) were grown on cover slips to confluence and pretreated with serum free medium for 30 min as described above. The cells were washed three times with phosphate buffered saline (PBS) containing 1 mM MgCl$_2$ and 0.1 mM CaCl$_2$ (solution A). The cells were fixed with 3% paraformaldehyde in solution A for 10 min, and permeabilized with 0.5% Triton X-100 in solution A for 5 min at room temperature. The cover slips were then washed 3 times for 5 min with solution A. Primary antibody (anti-cytochrome c) was used at a dilution of 2 μg/ml in PBS and applied for 1 h with gentle shaking. The cells were washed with PBS and a fluorescein isothiocyanate-conjugated anti-rabbit 1 g was applied for 1 h according to the manufacturer. The cover slips were washed, mounted on microscope slides, viewed and photographed on a Zeiss Axiovert 25 fluorescent microscope.

Analysis of P53/P56 Lyn Kinase Expression

Confluent cultures of AoSMC were incubated with ApoCI (2.5 µg/ml medium), ApoCIII (2.5 µg/ml medium), ApoCI-enriched HDL (1 µg apoA-I/ml medium), or apoA-I-poor HDL (5 µg apoA-I/ml medium). Cells were harvested in PBS at various time intervals and stored frozen in the presence of the protease inhibitor cocktail above. Western analysis for p53/p56 Lyn kinase was performed using primary anti-Lyn p53/p56 antibody (1:300) (Santa Cruz Biotechnology) and chemiluminescence (Amersham Pharmacia Biotech, Piscataway, N.J.).

Measurement of the Levels of Caveolin-I, Scavenger Receptor BI, and ABC Transporter ABCAI Confluent cultures of AoSMC were preincubated with serum-free medium for 30 min and then treated with ApoCI (2.5 µg/ml medium), HMS (58.8 µg apoA-I/ml medium and 6.2 µg ApoCI/ml medium), and C2-Ceramide (30 µM). At indicated time periods cells were harvested in PBS and pellets lysed in 10 mM HEPES buffer (pH 7.4) 5 mM EDTA, 0.25 mM EGTA, 50 mM NaF, 0.35 M sucrose, 0.1% Nonidet P-40 and protease inhibitors 2 µg/ml aprotinin, 10 µg/ml leupeptin, 5 µg/ml pepstatin, and 1 mM PMSF. Protein concentration was determined using BCA-kit (Pierce, Rockford, Ill.). 100 µg of protein was subjected to electrophoresis in denaturing conditions on 4-15% polyacrylamide gel and electro transferred onto nitrocellulose (BioRad, Rochester, N.Y.). After the transfer, membranes were blocked for 1 h at room temperature in TBS-T/5% milk. Western assay was performed using rabbit caveolin-I (1:1000), SR-BI (1:5000) or goat ABCA1 (1:1000) primary antibody (Santa Cruz Biotechnology, Santa Cruz, Calif.) and horseradish peroxidase-conjugated anti-rabbit or anti-goat antibody (Amersham Pharmacia Biotech, Piscataway, N.J.). Blots were developed using ECL$^{plus}$ Western blotting detection reagents (Amersham Pharmacia Biotech) and were scanned by laser densitometry. The intensity of the signals were quantified with the ImageGuant program (Molecular Dynamic, Sunnyvale, Calif.).

Example 1

ApoCI and ApoCI-Enriched HDL Particles Stimulate Apoptosis in ASMC

Cells incubated with ApoCI contained many apoptotic cells, as judged by white staining of the nucleus after treatment with 4',6-diamidino-2-phenylindole dihydrochloride (DAPI) reagent (FIG. 1A). In contrast, cells incubated with ApoCIII for 24 hours had only a few apoptotic cells (FIG. 1A). After fluorescence microscopic quantitative analysis of DAPI staining of the nucleus in attached cells after treatment (FIG. 1B), 2.24% of normal (control) cells, 4.78% of ApoCIII-treated cells, and 26.19% of ApoCI-treated cells were apoptotic. In addition, ~50% of ASMC incubated with ApoCI-enriched HDL particles were apoptotic; whereas only ~2% of the cells incubated with ApoCI-poor HDL were apoptotic (FIG. 1B; Table 1).

Apoptotic cells undergo endonucleosomal cleavage, resulting in the fragmentation of DNA into 180 to 200 basepair fragments that resolve as a ladder on agarose gel electrophoresis. Cells incubated with tumor necrosis factor α (TNF-α) (positive control), or with ApoCI, exhibited DNA laddering. In contrast, control cells, and those incubated with ApoCIII, did not exhibit significant DNA laddering (FIG. 1C).

Example 2

Neutral Sphingomyelinase Inhibitor GW4869 Abrogates ApoCI-Induced Apoptosis

Figure 2:
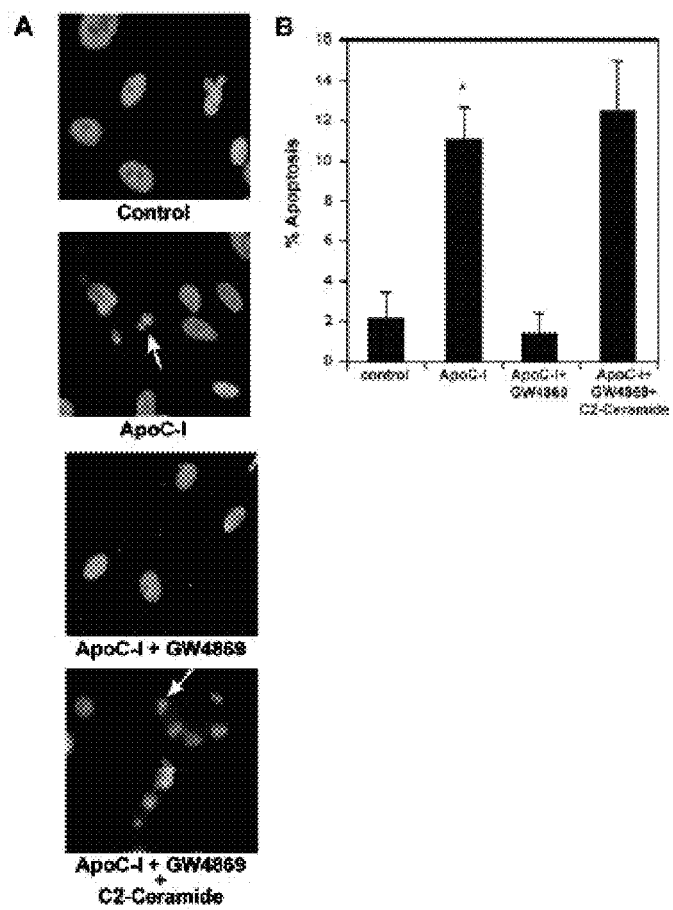
FIGS. 2A-2B depict the effect of ApoCI, the N-SMase inhibitor, GW4869, and C-2 ceramide on apoptosis in cultured human ASMC.

As shown in FIG. 2A and the corresponding densitometric scan (FIG. 2B), N-SMase inhibitor GW4869 (20 µmol/L) completely abrogated the ApoCI-induced apoptosis (~12% compared with control, ~2%), an effect that was also observed using a lower dose (10 µmol/L) of GW4869. However, when C2-ceramide was added to the ASMC with ApoCI and GW4869, the inhibitory effect of GW4869 on N-SMase was bypassed, and apoptosis was restored (FIGS. 2A and B) (~12.5% of apoptotic cells compared with control of 2.2% apoptotic cells).

Example 3

Figure 3:
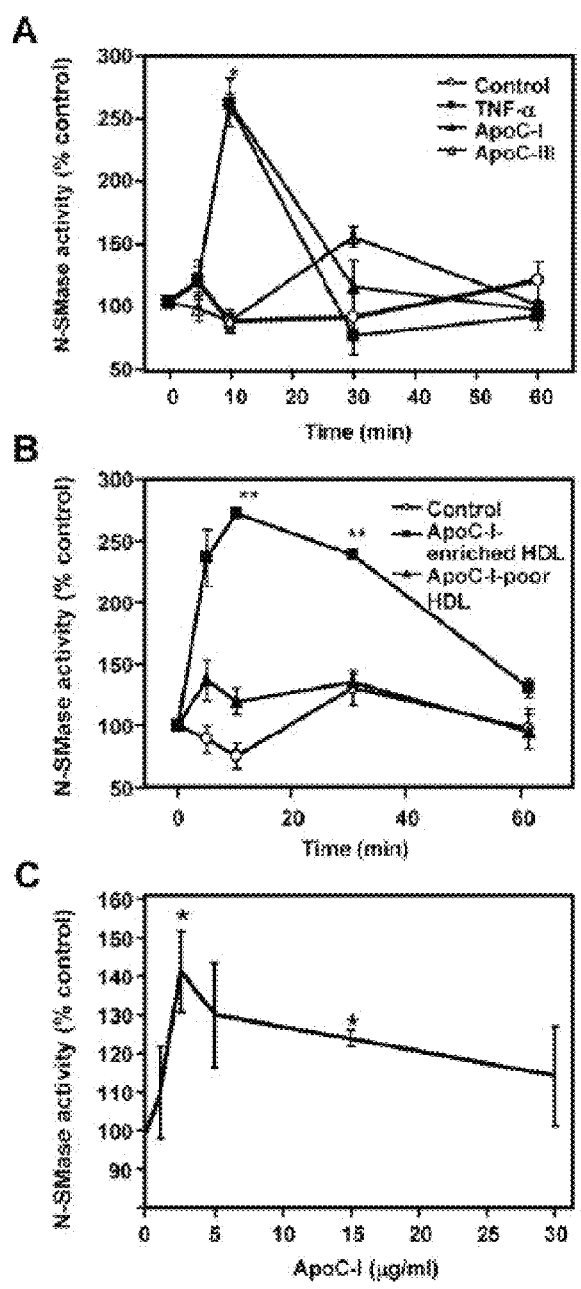
FIGS. 3A-3C depict the effects of ApoCI, ApoCIII, TNF-α, ApoCI-enriched HDL, and ApoCI-poor HDL on the activity of N-SMase in ASMC. Confluent cultures of ASMC were preincubated for 30 minutes with serum-free (control) medium, then ApoCI (2.5 µg/mL medium), ApoCIII (2.5 µg/mL medium), TNF-α (20 ng/mL medium) (FIG. 3A, top), or ApoCI-enriched HDL (1 μg apoAI/mL medium), or ApoCI-poor HDL (5 μg apoA-I/mL medium) (FIG. 3B, middle) were added individually to cells. The cells were then incubated and harvested at the indicated time points, and the activity was of N-SMase determined using [$^{14}$C]sphingomyelin as substrate. The N-SMase activity in control cells was 22 nmol/h per milligram cell protein, and this value was considered as 100% activity. In a separate experiment (FIG. 3C bottom), cells ($0.5 \times 10^5$) were seeded in P60 Petri dishes and grown in DMEM supplemented with 10% fetal bovine serum for 5 days. After preincubation of cells for 30 minutes in serum-free medium, increasing amounts of ApoCI were added. After incubation for 10 minutes, cells were harvested, and N-SMase activity was measured.

ApoCI and ApoCI-Enriched HDL Particles Stimulate the Activity of N-SMase in Cultured ASMC Within 5 minutes of incubation of cells with TNF-α (positive control) and ApoCI, there was ~2-fold increase in the activity of N-SMase that reached a maximum at 10 minutes and then decreased to baseline by 30 to 60 minutes (FIG. 3A). Such a pattern was not seen in the control cells or in those incubated with ApoCIII. The stimulation of N-SMase activity with ApoCI-enriched HDL particles was even more pronounced than that seen with TNF-α and ApoCI (FIG. 3B). At 5 minutes, there was a 2.6-fold stimulation of activity of N-SMase that reached a maximum of 2.7-fold stimulation at 10 minutes. In contrast to TNF-α and ApoCI, the stimulation of N-SMase activity with ApoCI-enriched HDL was still manifested (2.2-fold) at 30 minutes and then approached baseline at 60 minutes (FIG. 3B). ApoCI-poor HDL also stimulated N-SMase activity in a similar pattern, but to a considerably lesser extent than ApoCI-enriched HDL (FIG. 3B). ApoCI exerted a concentration-dependent increase in the activity of N-SMase in ASMC (FIG. 3C), with a maximum increase in N-SMase activity (1.5-fold) at a concentration of ApoCI of 2.5 µg/mL medium). In additional experiments to examine the specificity of this inhibitor, we found that GW4869 did not alter the acid sphingomyelinase activity (control: 400 nmol/mg protein; GW4869: 340 nmol/mg protein) in cultured human ASMC.

Example 4

Antibody Against N-SMase Abrogates ApoCI-Enriched HDL-Induced N-SMase Activity in Cultured ASMC Previous studies in human renal proximal tubular cells (Chatterjee, S. (1993) Adv. Lipid Res. 26:2548) and neuronal cells (Spence, M. W. (1993) Adv. Lipid Res. 26:3-23) have shown that N-SMase is localized on the outer leaflet of the plasma membrane. Using N-SMase antibody and FITC-conjugated secondary antibody, we made similar observations in human ASMC. We therefore preincubated ASMC with an antibody (IgG) against N-Smase (1:500 dilution) and found that anti-N-SMase, but not rabbit IgG (control), inhibited the stimulation of N-SMase activity by ApoCI-enriched HDL by 77%. This result suggested that ApoCI mediated the increased activity of N-SMase in human ASMC by the ApoCI-enriched HDL particle at the cell surface.

Example 5

Figure 4:
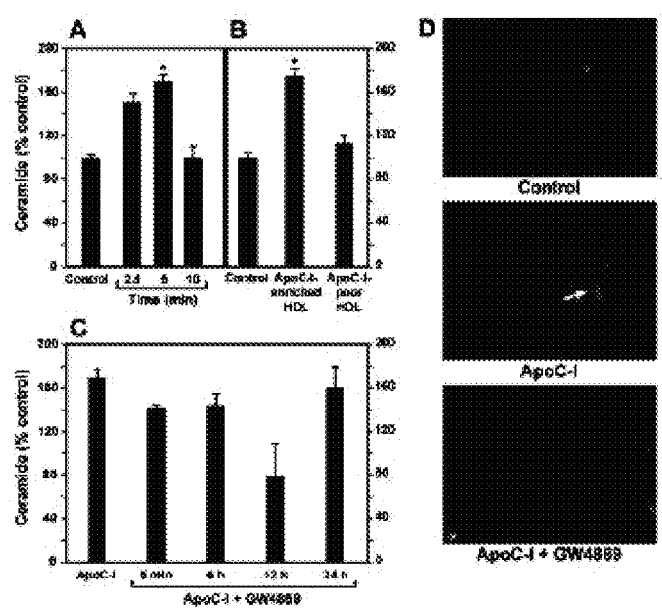
FIGS. 4A-4D depict the effect of ApoCI, ApoCI-enriched HDL, and ApoCI-poor HDL on the level of ceramide in ASMC. Confluent ASMC were incubated with ApoCI (2.5 μg/mL) with time (FIG. 4A, upper left) or with ApoCI-enriched HDL (1 μg apoA-I/mL medium) or ApoCI-poor HDL (5 μg apoA-I/mL medium) (FIG. 4B, upper right) for 30 minutes.

ApoCI and ApoCI-Enriched HDL Particles Stimulate the Generation of Ceramide in Cultured Human ASMC ApoCI exerted a time-dependent increase in ceramide levels, which reached a maximum effect (1.7-fold) by 5 minutes and then decreased to a value similar to that in control cells by 10 minutes (FIG. 4A). Incubation of ASMC with ApoCI-enriched HDL particles with time reached a maximum increase (~1.7-fold) in the level of ceramide by 30 minutes, compared with control cells, whereas ApoCI-poor HDL only stimulated the ceramide level slightly (FIG. 4B). GW4869 (20 μmol/L) significantly decreased the cellular level of ceramide induced by ApoCI after 5 minutes and 6 hours of incubation. GW4869 completely inhibited ApoCI-induced ceramide production after 12 hours of incubation but reversed it to a high level 24 hours later (FIG. 4C). Using an anti-ceramide antibody, cells treated with ApoCI reacted strongly, as judged by immunofluorescence microscopy, compared with control cells (FIG. 4D). Most fluorescence was localized in the perinuclear area, an effect of ApoCI on the ceramide level that was eliminated by GW 4869, an inhibitor of N-SMase.

Example 6

Figure 5:
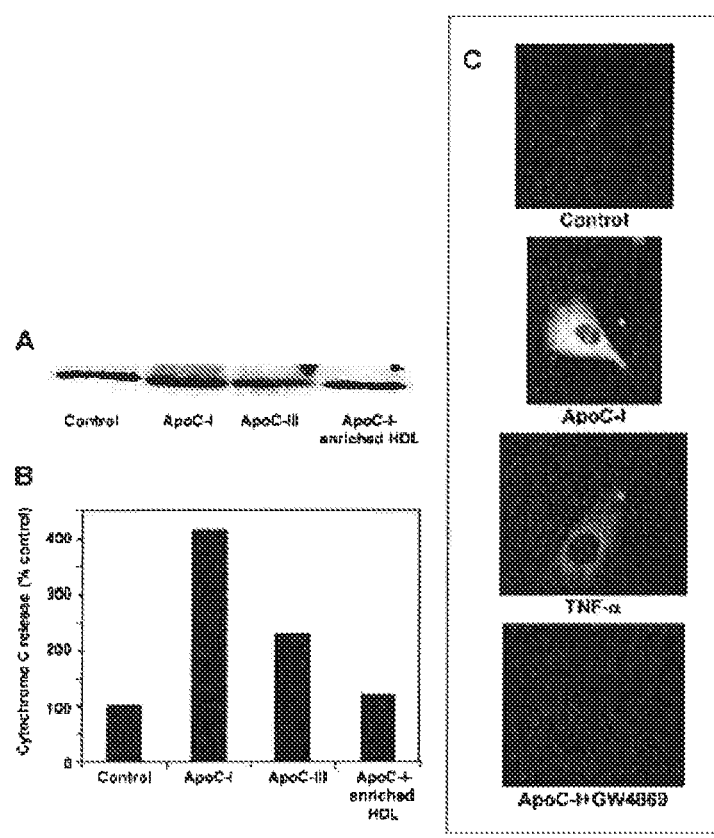
FIGS. 5A-5C depict the effect of ApoCI, ApoCIII, ApoCI-enriched HDL, and GW4869 on cytochrome c release in ASMC. After treatment of confluent cells for 24 hours with ApoCI (2.5 μg/mL medium), ApoCIII (2.5 μg/mL medium), or ApoCI-enriched HDL (1 μg apoA-I/mL medium), the cells were lysed. The cell lysate was used as the source of cytochrome c, and the pellet was used as a source of caspase-3. The cell lysates were separated by SDS-polyacrylamide gel electrophoresis, blotted onto nitrocellulose, and cytochrome c detected using a polyclonal antibody against cytochrome c (FIG. 5A, top panel). The gels were then subjected to densitometric scanning (FIG. 5B, middle panel). In a separate experiment (FIG. 5C, right), confluent cells were grown on cover slips and pretreated with serum-free medium for 30 minutes. The cells were then incubated with control medium, ApoCI (2.5 μg/mL medium), TNF-α (20 ng/mL), or ApoCI (2.5 μg/mL)+GW4869 (20 μmol/L) for 24 hours. The cells were then washed, treated with a primary anti-cytochrome c antibody, washed with phosphate-buffered saline, and treated with a fluorescein isothiocyanate-conjugated anti-rabbit IgG (FIG. 5C, lower panel).

ApoCI and ApoCI-Enriched HDL Particles Stimulate the Release of Cytochrome c from Mitochondria in ASMC The release of cytochrome c from mitochondria into cytosol is a key pro-apoptotic event. ApoCI stimulated the release of cytochrome c 4.1-fold. ApoCIII and ApoCI-enriched HDL particles also showed some stimulation of cytochrome c (2.3- and 1.2-fold, respectively) (FIGS. 5A and B). Using immunofluorescence, a marked increase in the release of cytochrome c from mitochondria into the cytoplasm with ApoCI (even greater than that with TNF-α) was noted, an effect that was inhibited by GW4869 (FIG. 5C).

Example 7

ApoCI and ApoCI-Enriched HDL Particles Stimulate the Expression of Caspase-3 in Human ASMC ApoCI stimulated the caspase-3 level 4-fold compared with control medium. ApoCI-enriched HDL stimulated caspase-3 expression in ASMC 1.7-fold, whereas ApoCI-poor HDL did not. ApoCIII also stimulated caspase-3 expression, but to a lesser extent than ApoCI-enriched HDL.

Material and Methods

The following materials and methods were used in Examples 8-9

Study Protocol

All animal studies were performed under approved protocol by the Animal Care and Use Committee of the Johns Hopkins University, Baltimore, Md. Animals (purchased from Covance Research Products, Denver, Pa.) consisted of three sets of different atherosclerotic stages (group 1: three WHHL rabbits, group 2: six WHHL rabbits fed with high fat 14% coconut oil and 0.2% cholesterol diet for 3 months, group 3: five WHHL with similar diet but additional balloon-induced endothelial denudation).

We acquired MR angiography and vessel wall imaging on a 1.5 T whole body MR scanner. During scanning animals were anaesthetised with ketamine (25 mg/kg bodyweight IM), xylazine (2.5 mg/kg bodyweight IM), and acepromazine (0.75 mg/kg bodyweight IM). Mean anaesthesia time per animal was 2.5 hours. Snake venom (Russell's viper, 0.15 mg/kg intra-peritoneal) followed by histamine (0.02 mg/kg intravenous) were administered to all animals twice within 48 hours). All supplies were from Sigma Chemical Co, St. Louis, Mo.

MR imaging was repeated after 2 days in 10 animals at exact locations by registration against the baseline study employing anatomical landmarks.

After the second MRI, animals were euthanized (pentobarbital (100 mg/kg i.v.), the aorta excised and sectioned into equal sized samples for histopathologic and immunohistochemical analysis.

MRI and Image Analysis

Sub-renal aortic MRI angiography and vessel wall imaging were performed on a commercial 1.5 Tesla (T) whole body MR system (Gyroscan ACS-NT, Philips) after developing a novel vector ECG triggered 3D radial balanced Fast-Field-Echo (FFE) angiography gradient sequence (TR=7.2 ms, TE=3.6 ms, FOV=360 mm, matrix=512*512, reconstructed voxel size=0.7*0.7*1.5 mm). Orthogonal to prior angiography, we acquired 80-100 transverse concomitant slices of a fat suppressed high resolution 3D black-blood FSE imaging sequence (TR=3 heart beats, TE=10.5 ms, ETL=18, Inversion time (TI)-400 ms, FOV=76 mm, Matrix=304*304, slice thickness=2 mm) to cover entirely the sub-renal aorta to its iliac bifurcation. For quantitative measurements we analysed signal-to-noise ratios (SNR=Signal intensity$_{blood}$/SD$_{Air}$) with a previously described analysis software (Constantinides, P. and Chakravarti, R. N. (1961) Arch Pathol. 72:197-208).

Comparison of Histology and MR Images

In animal groups of plaque rupture, Hematoxylin and eosin (HE) stained tissue samples were analysed with an Axioskop microscope and an Axiocam digital camera (Carl Zeiss, Germany) by one observer. Six measurements were taken per histological slice in which measurement locations were marked on the image for exact matching with the MRI slice.

According to the anatomical specimen coordinates (distance from right renal artery and iliac bifurcation) equivalent transverse MRI images were obtained to match MRI thickness measurements with equivalent histological locations.

Immunohistology

We stained sections fixed with Tissue-Tec-O.C.T. compound with Oil-Red-O. The formalin-fixed, paraffin-embedded blocks of tissues fixed with 10% buffered formalin solution were cut into 4 μm thick slides onto chemmate slides and subjected to immunohistochemical analysis with antibody against ApoCI (goat anti-human ApoCI antibody, Academy Bio-Medical Co, Houston, Tex.), ceramide (IgM-enriched mouse anti-ceramide, Glycobiotech, Kuekels, Germany), caspase-1 and caspase-3 (rabbit anti-human, Santa Cruz, Calif.), CD-68 and β-actin (mouse monoclonal, Cell Marque/ Ventara Laboratory, Tucson, Ariz.). The indirect immunoperoxidase method using 3-amino-9-ethylcarbazole or vector Nova Red (Vector Laboratories, Calif.) with Hematoxylin counterstaining was used.

Tissue sections were also stained for apoptosis using 4',6-diamidino-2-phenylindole dihydrochloride reagent (DAPI). The activity of neutral sphingomyelinase in tissue extracts was carried out employing [$^{14}$C] sphingomyelin (American Radiolabelled Compounds, St Louis, Mo.) as a substrate as described (Kolmakova A. et al. (2004) Arterioscler Thromb Vasc Biol. 24(2):264-269). The immunocytochemical slides were analyzed and documented by a cardiovascular cytopathologist.

Statistics

Data comparisons and correlations were made by ANOVA and were reported as mean±1 SD whereas a value of P=0.05 was considered significant.

Example 8

MRI

Figure 6:
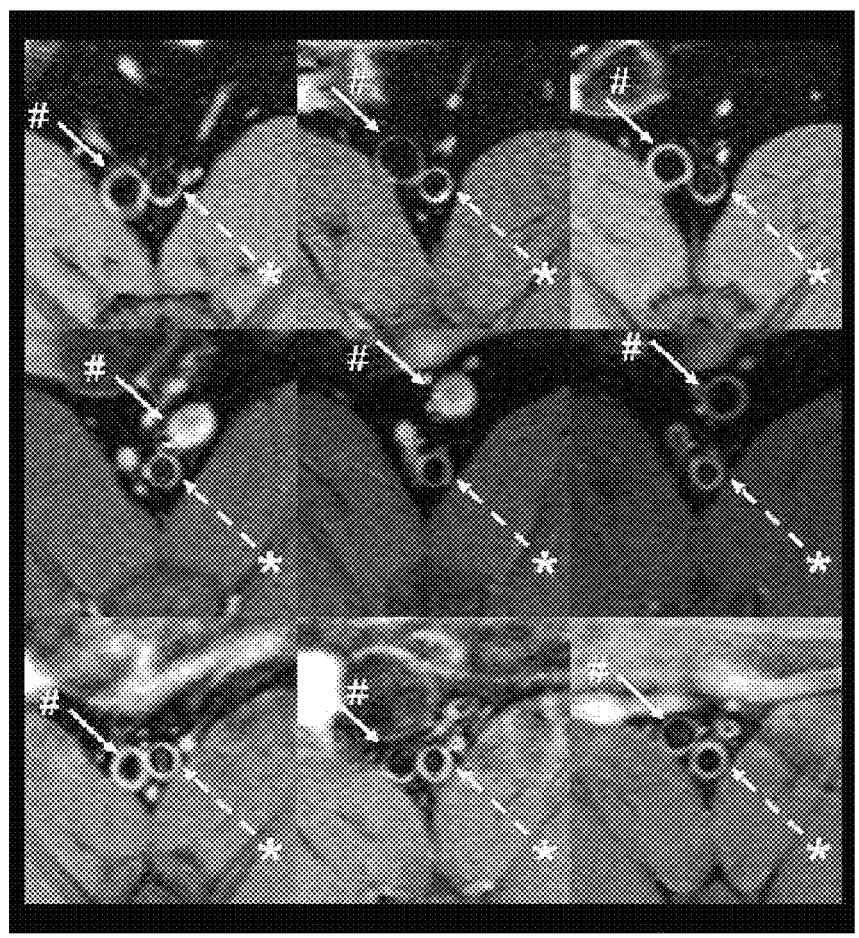
FIG. 6 depicts representative 3D FSE MRI aortic vessel wall images for three animal groups. MRI vessel wall images of group I-III on three comparable anatomic levels (A-C) of the sub-renal aorta (dashed arrows) demonstrate excellent image quality. Focal and general vessel wall thickening can be documented in all groups at all levels. Note the variable anatomic position of the inferior vena cava (solid arrows) and the variable venouos wall thickening due to slow flowing blood artifacts.

Sub-renal MRI angiography and vessel wall images with in-plane resolution up to 130 µm were consistently obtained in all animals at different anatomic levels of the aorta (FIG. 6).

The SNR of the three groups (FIG. 7A) was in the same range (39-52). Interestingly, cholesterol fed animals from group 2 compared to group 3 had significantly lower SNR (p=0.048), and compared to group 1, it shows a trend to significantly lower SNR (p=0.06).

Figure 7:
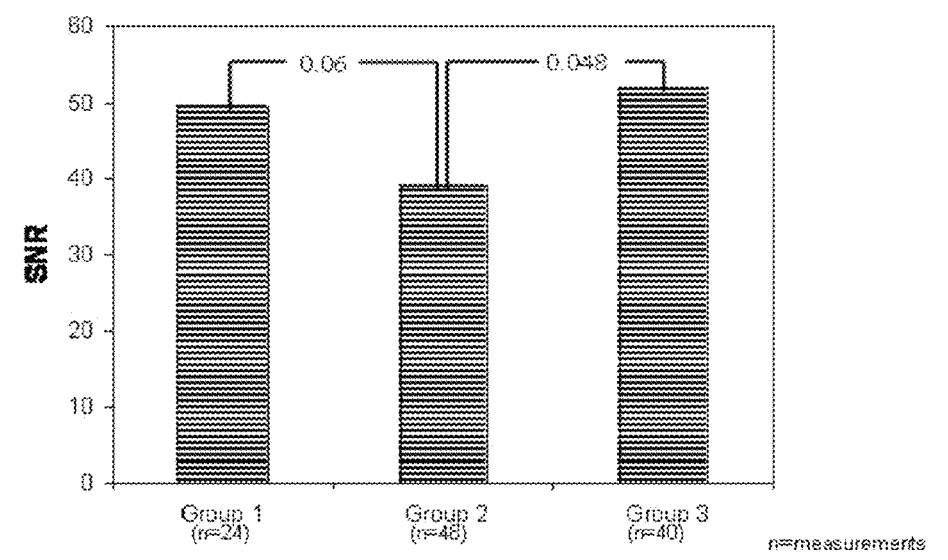
FIGS. 7A-7B depict SNR and vessel wall thickness correlation between histology and MRI.
Figure 7:
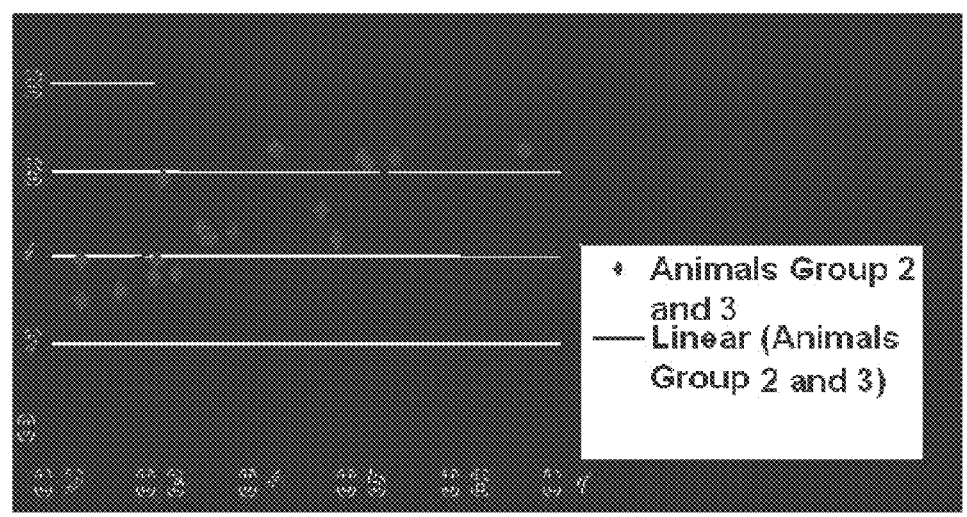

MRI vessel wall thickness in animal groups of plaque rupture (mean=0.42±3 mm) correlated well with histopathologic examination (y=0.81x+0.17, $R^2$=0.64, r=0.8, FIG. 7B).

We consistently found an inverse correlation between serum cholesterol levels (mg/dl) and vessel wall MRI signal (y=−4.9872x+1953.7; $R^2$=0.58, r=0.76, FIG. 8C).

Figure 8:
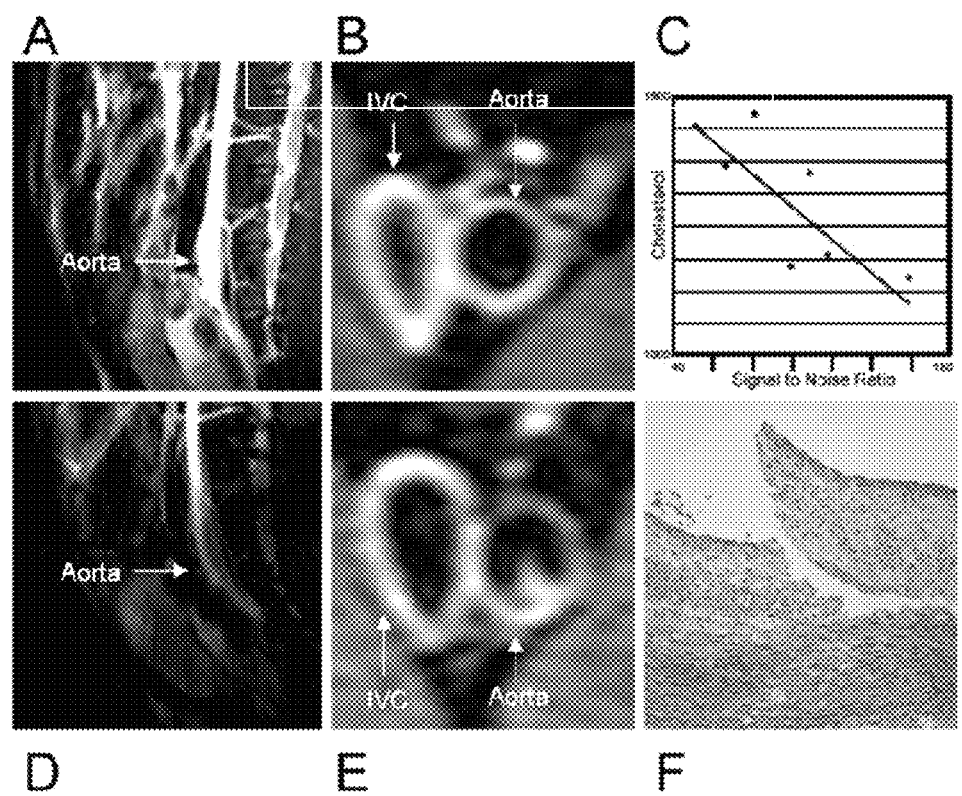
FIGS. 8A-8F depict aortic wall imaging with plaque rupture and corresponding histological flap. Sub-renal sagittal rabbit aortic MR angiography with corresponding axial FSE-vessel wall imaging (Aorta=sub-renal aorta, IVC=inferior vena cava) before (FIGS. 8A and 8B) and after (FIGS. 8D and 8E) snake venom and histamine administration. Note the high in-plane vessel wall image resolution of 130-250 μm (FIGS. 8B and 8D). The neo-intimal dissection visualised by MR in vivo (FIG. 8E) correlated well with histopathologic detection of ruptured atherosclerotic plaque (FIG. 8F).

Applying 3D high resolution angiography and vessel wall imaging before (FIGS. 8A and 8B) and after venom application (FIGS. 8D and 8E) to all rabbits, MRI was able to detect in vivo neo-intimal disruption with concomitant severe thrombosis (>40% stenosis) in six animals of groups 2 and 3 only (FIGS. 8D-8F).

Example 9

Immunohistology

Figure 9:
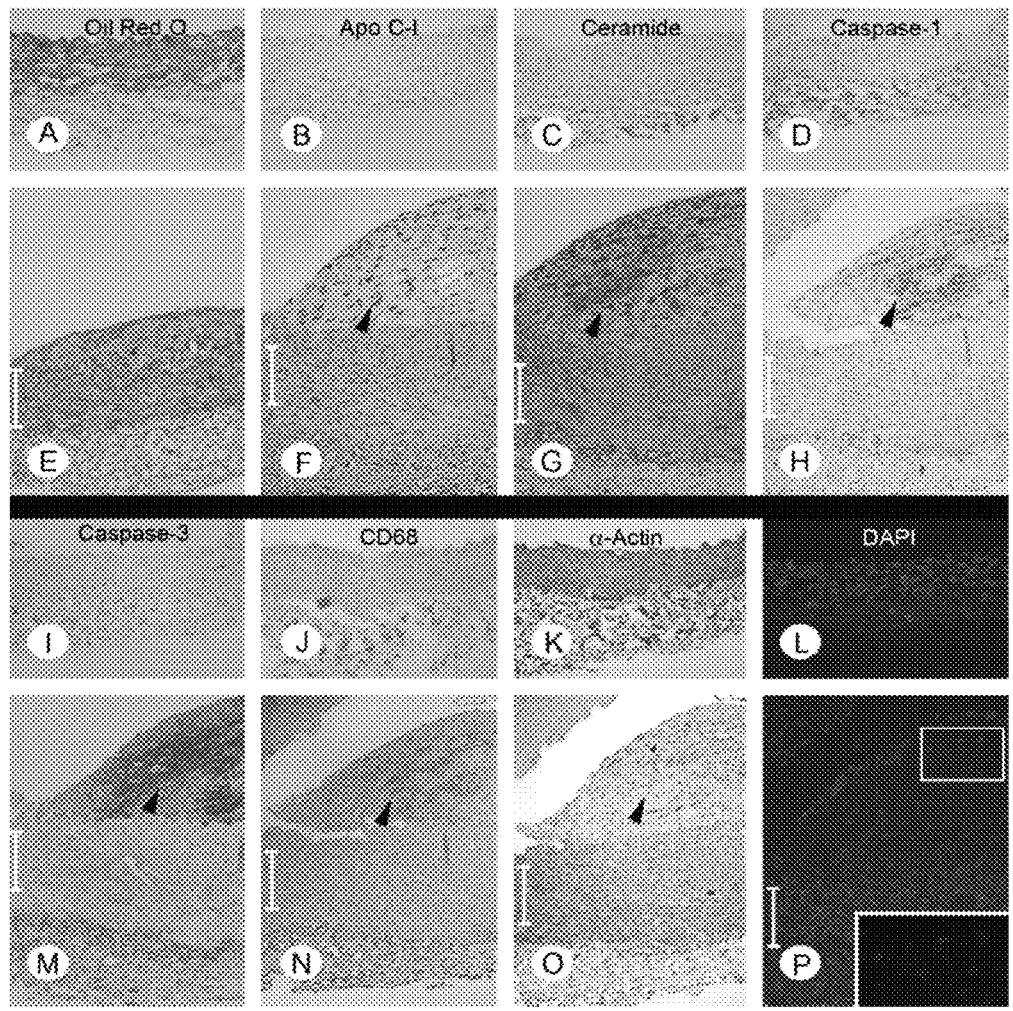
FIGS. 9A-9P depict immunohistochemical analysis of apoptotic markers in atherosclerotic lesions post venom. Representative immunohistochemical stainings from animals of group 1 (FIGS. 9A-9D and 9I-9L) and group 2 with a ruptured plaque (FIGS. 9E-9H and 9M-9P). Note the strong positive immunohistochemical staining in the group 2 animals adjacent to the ruptured plaque shown in FIG. 8 for ApoCI (FIG. 9F), ceramide (FIG. 9G), caspase-1 (FIG. 9H), caspase-3 (FIG. 9M). See spots indicated by arrows (FIGS. 9N and 9O) documenting macrophages, ASMCs and a few apoptotic cells in the group 2 animals adjacent to the ruptured plaque.

Group 2 rabbits exhibited strongly Oil Red 0 (ORO) positive plaque having large oil droplets (FIG. 9E) and pronounced immuno-histochemical staining of the aortic intima with the ApoCI antibody (FIG. 9F, see spots indicated by arrow) as opposed to group 1 rabbits (FIGS. 9A and 9B). When observed under a higher magnification, most, if not all the ApoCI from group 2 were found with the aortic smooth muscle cells and in macrophages. Next, we investigated the immuno-localization of ceramide, an apoptotic agent, previously shown to mediate ApoCI TNF-α and stress induced apoptosis. Group 2 rabbit aorta sections contained ceramide in the intima with massive deposits in the intimal plaque area (indicated by an arrow) and media but with less intensity (FIG. 9G), whereas group 1 animals only showed discrete ceramide staining in the media (FIG. 9C).

Immuno-staining with caspase-1 (FIGS. 9D and 9H) and caspase-3 antibody (FIGS. 9I and 9M) in group 1 and 2 animals showed its presence in the cytoplasm in the medial SMC but in sharp contrast strong and massive caspase-3 immuno-staining was observed predominantly in the neo-intimal area of dissection/plaque rupture (FIG. 9M) whereas, group 1 animals only had mild caspase-3 staining (FIG. 9I). In fact, no significant differences in the caspase-3 immuno-staining in the media of both groups of animals were observed.

To determine the cell type present in plaque intima the tissue sections were stained with CD-68 for macrophages and indeed these cells appeared to be among the predominant type of cells in the neo-intimal plaques (FIG. 9N, see arrow). No CD-68 positive macrophages were observed in control tissue (FIG. 9J) and in media (FIG. 9N). Also, strong β-actin staining (marker for smooth muscle cells) was observed in the neo-intima (FIG. 9O) and in the media in the control group of rabbit tissue. Study with DAPI reagent revealed the presence of some apoptotic cells in group 2 of rabbit sections (FIG. 9P, also see inset).

Figure 10:
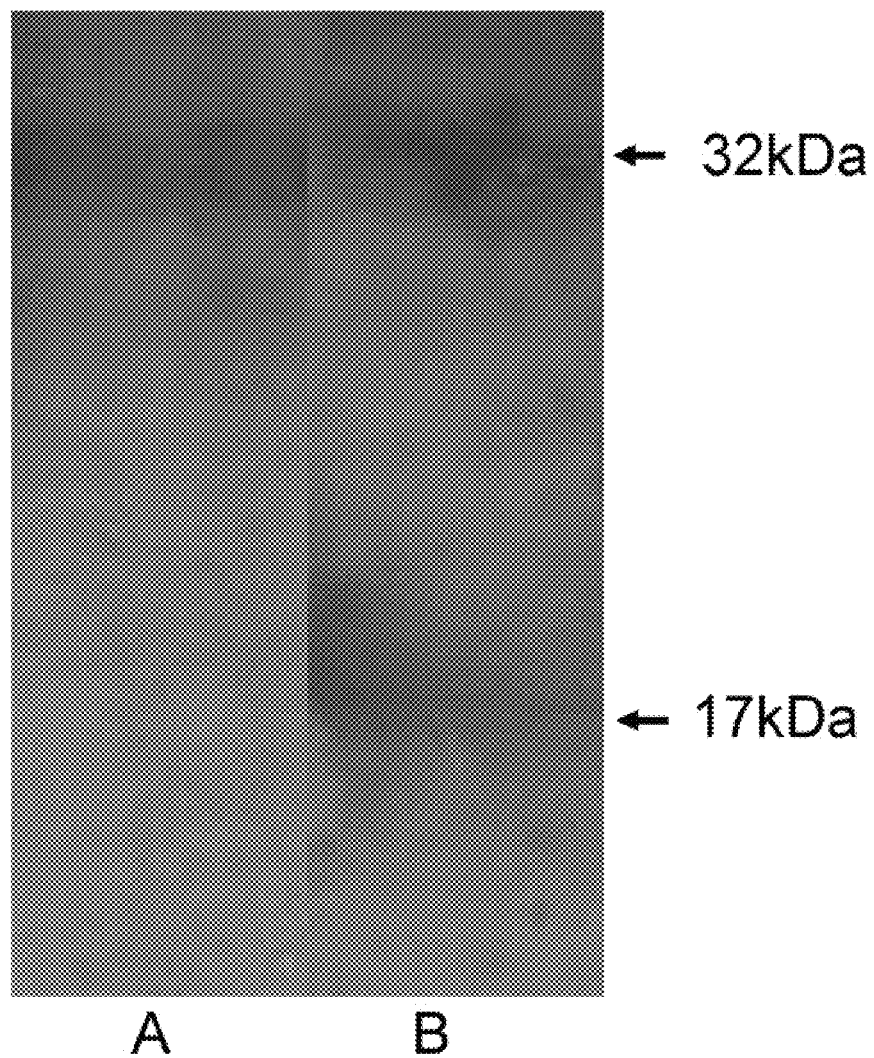
FIGS. 10A-10B depict representative immunoblot assay of caspase-3 in rabbit aorta sections. Proteins (50 μg per line) from homogenate of aorta sections were separated using 4-15% SDS-poly-acrylamide gel electrophoresis and transferred onto nitrocellulose-membrane. Western assay was performed using rabbit anti-human caspase-3 antibody.

Western immunoblot assay revealed the presence of both caspase-1 and caspase-3 in the rabbit tissue sections. In fact, the basal level of pro-caspase-3 (32 kDa) was similar in group 1 and 2 rabbit aorta sections (FIGS. 10A and 10B). However, the level of the active form of caspase-3 (17 kDa protein) was markedly increased in group 2 of rabbit aorta sections (FIG. 10B) compared to group 1 (FIG. 10A). Biochemical assay revealed that the activity of neutral sphingomyelinase in group 2 rabbits aorta sections was 2.5±0.5 fold higher than group 1 rabbit tissue sections (control tissue activity: 5 nmol/mg protein/hr).

In animals of group 3 with fat diet and endothelial denudation we observed accumulation of ApoCI, ceramide and caspase-3 more prominently in the vessel media.

Materials and Methods

The following materials and methods were used in Examples 10-15.

Patient Population

The group of 163 infants (31 white males, 39 white females; 47 black males and 46 black females) studied was previously characterized (Kwiterovich Jr P O. et al. (In press, 2004) Ethn. Dis.). There were 23 small-for-gestational age (SGA) infants, defined as a birth weight for gestational age <or =10% (Kwiterovich Jr P O. et al. (In press, 2004) Ethn. Dis.). The Joint Committee on Clinical Investigation at Johns Hopkins approved the study.

Lipid, Lipoprotein and Apolipoprotein Measurement

Plasma from cord blood was analyzed for levels of cholesterol, triglycerides, LDL and HDL cholesterol, Lp (a) lipoprotein, and apolipoproteins A-I, A-II, B, C-I, C-III, and apoE (Kwiterovich Jr P O. et al. (In press, 2004) Ethn. Dis.; Kolmakova A. et al. (2004) Arterioscler. Thromb. Vas. Biol. 24:1-9). Fifteen lipoprotein subclasses, the number of LDL particles, and the average sizes (nm) of VLDL, LDL and HDL were determined by nuclear magnetic resonance (NMR) spectroscopy (Kwiterovich Jr P O. et al. (In press, 2004) Ethn. Dis.; Otvos, J D. (2000) In: Rifai N. et al., Eds. Handbook of Lipoprotein Testing. Washington, D.C.:AACC Press, 609-623). Lipoprotein density profiles for VLDL, LDL and HDL were obtained after sucrose density gradient ultracentrifugation (DGU) (Macfarlane R D. et al. (1997) Electrophoresis 18:1796-1806; Farwig Z N. et al. (2003) Anal Chem 75:3823-3830).

Preparation of Lipoprotein Fractions from Sucrose DGU for Capillary Electrophoresis Fractions from the lipoprotein density profile were thawed and a portion subjected to delipidation (Macfarlane R D. et al. (1997) Electrophoresis 18:1796-1806; Farwig Z N. et al. (2003) Anal Chem 75:3823-3830). The samples were analyzed in duplicate by capillary electrophoresis using the Beckman P/ACE 5510 instrument at 17 kV for 30 minutes.

Preparation of Lipoprotein Fractions for MALDI-TOF Mass Spectrometry (MS) and Immobilized pH Gradient (IPG) Isoelectric Focusing (IEF)

The lipoprotein fractions were thawed, centrifuged to pellet particulate matter, and subjected to solid phase extraction delipidation (Macfarlane R D. et al. (1997) Electrophoresis 18:1796-1806; Farwig Z N. et al. (2003) Anal Chem 75:3823-3830). The apolipoproteins were eluted, concentrated, and an aliquot taken for MALDI-TOF MS analysis, using a Voyager Elite XL DE mass spectrometer. The remaining samples were evaporated to dryness, reconstituted in 250 µl 8.0 M urea containing 2% CHAPS, sonicated, degassed, and electrophoresis performed using the IPG phor unit (Amersham Pharmacia, Sweden) as described (Macfarlane R D. et al. (1997) Electrophoresis 18:1796-1806; Farwig Z N. et al. (2003) Anal Chem 75:3823-3830).

Activity of Cholesterol Ester Transfer Protein

CETP activity was determined by using the CETP Activity Kit by Roar Biomedical, Inc. (New York, N.Y.), according to the manufacturer's specifications.

Statistical Methods

The relationships between lipids, lipoprotein cholesterols, apolipoproteins, lipoprotein subclasses and lipoprotein sizes in the four groups of infants were evaluated, first using ANOVA on data that were not adjusted for age, and then linear regression to correct for influence of gestational age. P values were also estimated using the Kruskal-Wallis test, due to the small size of two of the groups (n=5 each in group 0 and 3). To evaluate differences in these lipid-related variables between white and black and male and female infants, a CHI squared test was performed. All p values found to be significant at the $p<0.05$ levels.

Example 10

Lipoprotein Density Profiling after Sucrose DGU

Figure 11:
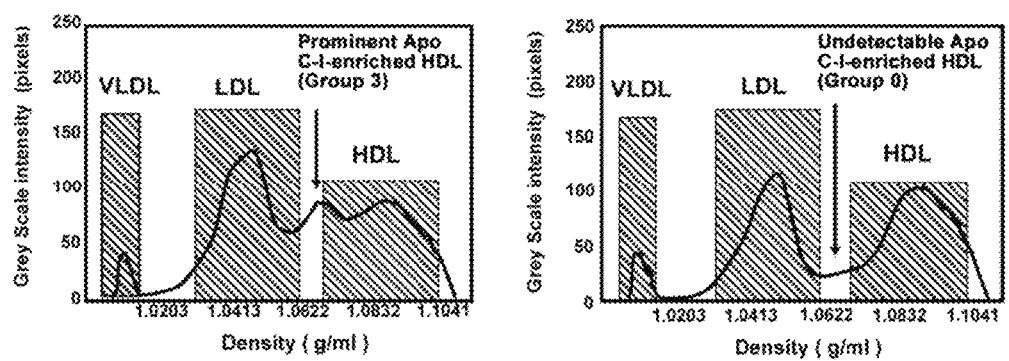
FIG. 11 depicts lipoprotein profiles from cord blood obtained after sucrose density gradient ultracentrifugation. The profile on the left is from a group 3 infant while that on the right is from a group 0 infant.

A prominent feature of the lipoprotein density profiles was the presence or absence of a distinct peak of d 1.062 and 1.072 g/ml between the major peaks for LDL and HDL (FIGS. 11A, 11B). The peak density of Lp (a) in adult plasma is close to 1.055 gm/ml, and thus potentially occurring within the density range between 1.062 and 1.072 gm/ml. Lp (a) levels in cord blood, however, are very low (Kwiterovich Jr P O. et al. (In press, 2004) Ethn. Dis.), and the mean Lp (a) levels (mg/dL+/−1 SD) in group 3 (1.2+/−1.3)) and group 0 (0.6+/− 0.9) were not significantly different.

Example 11

Characterization of Lipoprotein Peak of d 1.062-1.072 g/ml

Two infants from group 3 and group 0, respectively, were selected for detailed analyses of this lipoprotein peak. The Lp (a) levels in these two infants were low (3 mg/dL in 013 and undetectable in 021). Three lipoproteins, namely, LDL, the lipoprotein with a peak of d 1.062-1.072 g/ml, and HDL, were isolated by sucrose DGU, delipidated and prepared for the following analyses.

Capillary electrophoresis and isoelectric focusing (IEF).

After capillary electrophoresis, apoA-I (47.7%) was the major apolipoprotein in the lipoprotein of d 1.062-1.072 g/ml from the group 3 infant, and ApoCI, ordinarily a minor component of HDL, was the second most prevalent apolipoprotein (37.6%). Negligible amounts of apolipoproteins were detected in the same lipoprotein density segment from the group 0 infant. These results were confirmed by IEF, showing clearly apoA-I (pI 5.43) and ApoCI (pI 6.70) bands in the prominent lipoprotein peak from the group 3 infant, but not the group 0 infant.

MALDI-TOF MS Analyses.

Figure 12:
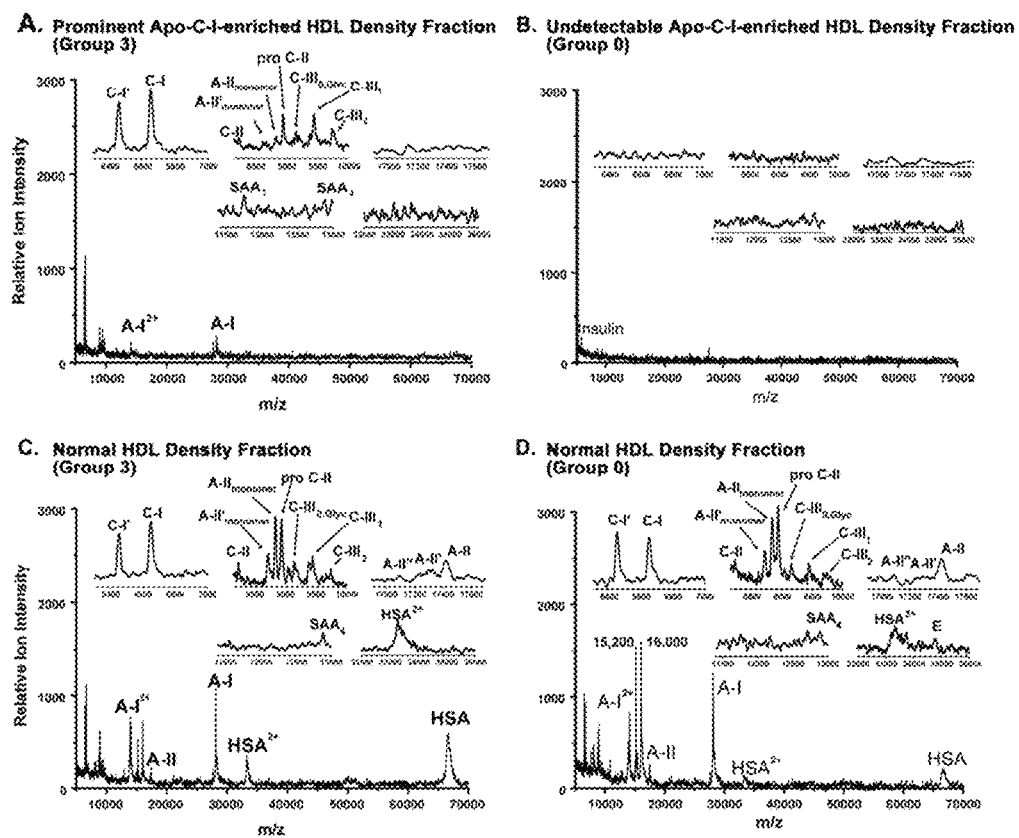
FIGS. 12A-D depict MALDI-TOF MS of ApoCI-enriched HDL and normal HDL. ApoCI-enriched HDL (panels A and B) and normal HDL (panels C and D) were isolated from plasma of a group 3 infant (loft panels A and C) and group 0 infant (panels B and D) and prepared for MALDI-TOF MS.

In the prominent lipoprotein peak of d 1.062-1.072 g/ml (FIG. 12A) from the group 3 infant, the intensity of ApoCI, relative to the intensity of apoA-I, was notably greater than in HDL (FIG. 12C). The apolipoproteins in the lipoprotein peak of d 1.062-1.072 from the group 0 infant were barely detectable (FIG. 12B). There was little difference in the spectra for HDL of usual density between the group 3 (FIG. 12C) and the group 0 infants (FIG. 12D). The above observations were confirmed in another group 3 infant and a normal control. There was no difference detected in LDL spectra.

Gradient Gel Electrophoresis of HDL.

Figure 13:
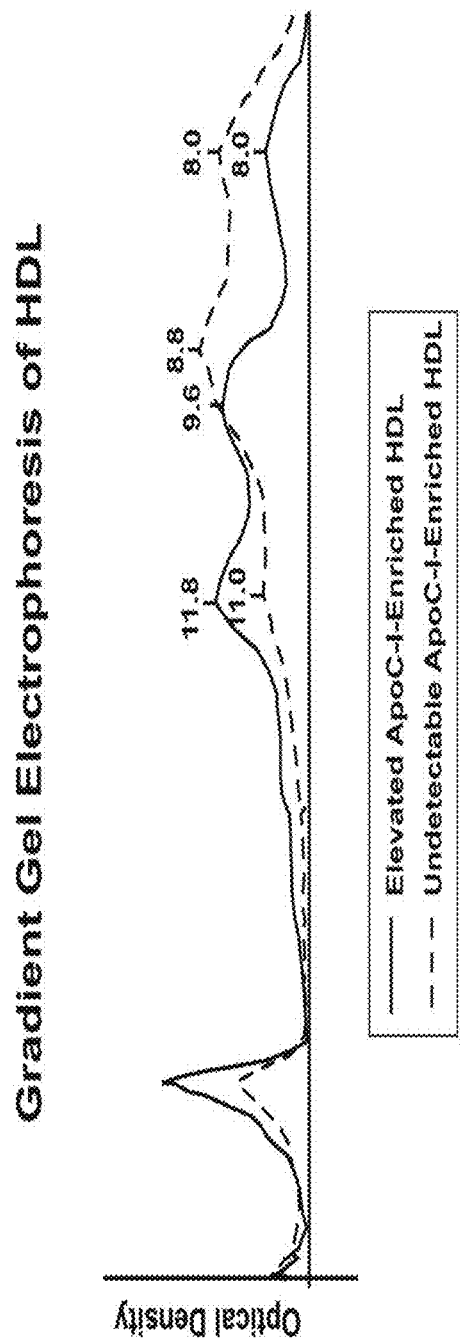
FIG. 13 depicts gradient gel electrophoresis of HDL. Plasma lipoproteins were isolated by ultracentrifugation at d>1.21 g/ml and prepared for GGE. Following GGE, gels were stained for protein and densitometric scans performed. Scans of HDL from a group 3 infant are depicted by the solid line and from a group 0 infant by the broken line. Sizes of the HDL subclasses are shown in nm.

Plasma from four infants in group 3, one infant in group 2, and three infants in group 0 were ultracentrifuged at d<1.21 g/ml and GGE performed (Nichols A. et al. (1991) Biochem et Biophys Acta. 1085:306-14; Genzel-Boroviczeny O. et al. (1988) Pediatr. Res. 23:543-547). As shown in representative densitometric scans of the gels (FIG. 13), group 3 infants differed from group 0 infants. The largest HDL subclass in group 3 infants had a mean diameter of 11.6 nm (range 11.5 to 11.8), compared to 9.4 (range 8.8 to 10.8) in group 0 infants, and 10.8 in one group 2 infant.

ApoCI was found in each of different HDL subclasses (FIG. 13), as judged by immunoblots of the GGE gels using an anti-ApoCI antibody. These results are consistent with those from MALDI-TOS MS (see above), and indicate that all HDL subclasses contained ApoCI.

Example 12

Immunochemical Characterization of the Apolipoproteins in Infants with Prominent Versus Undetectable Amounts of the Lipoprotein of d 1.062-1.072 g/ml The distribution of apolipoproteins A-I, A-II, B, C-L and C-III, between apoB-containing lipoproteins (VLDL, DL, LDL and Lp (a)), and non-apoB-containing lipoproteins (HDL) was determined without prior ultracentrifugation in infants from group 3 (N=5) and group 0 (N=5). The apoB-containing lipoproteins in one ml plasma were precipitated with heparin-manganese chloride, and the apolipoprotein levels measured in plasma, heparin-manganese supernatants (non-apoB containing lipoproteins) and resolubilized precipitates (apoB-containing lipoproteins), using rocket immunoelectrophoresis (Kolmakova A. et al. (2004) Arterioscler. Thromb. Vas. Biol. 24:1-9).

Apolipoprotein B.

The plasma levels of total apoB were higher in group 3 than in group 0 infants, but did not reach statistical significance (Table 2). All of the apoB was in the heparin manganese precipitates and none was detected in the supernatants.

Apolipoprotein C-I.

The mean levels of ApoCI in both whole plasma and the heparin-manganese supernatants were about twofold higher in group 3 than in group 0 infants (Table 2). In a larger group of infants, the mean (SD) plasma level of ApoCI (µmol/L) of 11.6 (4.8) in 17 group 3 infants was significantly higher (p=0.036) than that of 7.7 (4.7) in 13 infants from group 0. All of the ApoCI was in the supernatants and absolutely none was detected in the precipitates, distinctly different than later in life when a significant portion of ApoCI is associated with the apoB-containing lipoproteins (Curry M D. et al. (1981) Clin Chem 27:543-548). These immunochemical results further indicate that the ApoCI-enriched lipoprotein peak is an HDL subclass rather than a LDL subclass.

Apolipoprotein C-III.

Infants in group 3 had significantly more of their ApoCIII associated with the non-apoB-containing lipoproteins, while infants in group 0 had significantly more of their ApoCIII associated with the apoB-containing lipoproteins (Table 2).

Apolipoproteins A-I and A-II.

The apoA-I levels were higher in both the supernatants and precipitates in the infants in group 3 than in group 0 (Table 2). The mean apoA-II levels between groups 3 and 0 were very similar for whole plasma, supernatants and precipitates (Table 2).

Apolipoprotein E.

In a separate experiment, the concentration (μmol/L) of apoE in group 3 infants was higher than in group 0 infants in pooled whole plasma (3.8 v 1.7) and heparin-manganese supernates (2.3 v 1.4).

Definitions of Four Groups of Infants.

Using lipoprotein density profiles (FIG. 11), four groups of infants were classified, based on the gray intensity scale in the area between LDL and HDL: Group 0, no inflection above baseline (no detectable ApoCI-enriched HDL); Group 1, small inflection (blip) above baseline (1 to 5 on scale) (possible ApoCI-enriched HDL); Group 2, a peak above baseline >5 and <50 on scale (probable ApoCI-enriched HDL; Group 3, a large peak above baseline >50 on scale (prominent ApoCI-enriched HDL).

Example 13

Lipid, Lipoprotein, Apolipoprotein and Lipoprotein Subclasses and Lipoprotein Sizes in Group 0, 1, 2, and 3 Infants Lipoprotein density profiling was performed in 156 of the 163 infants (95.7%) previously reported (Kwiterovich Jr P O. et al. (In press, 2004) Ethn. Dis.), to determine the frequency of appearance and degree of enrichment of the d 1.062-1.072 g/ml peak. The frequency (%) of the four groups was: 0, 17.3%; 1, 41.0%; 2, 22.4%; and 3, 19.2%.

Figure 14:
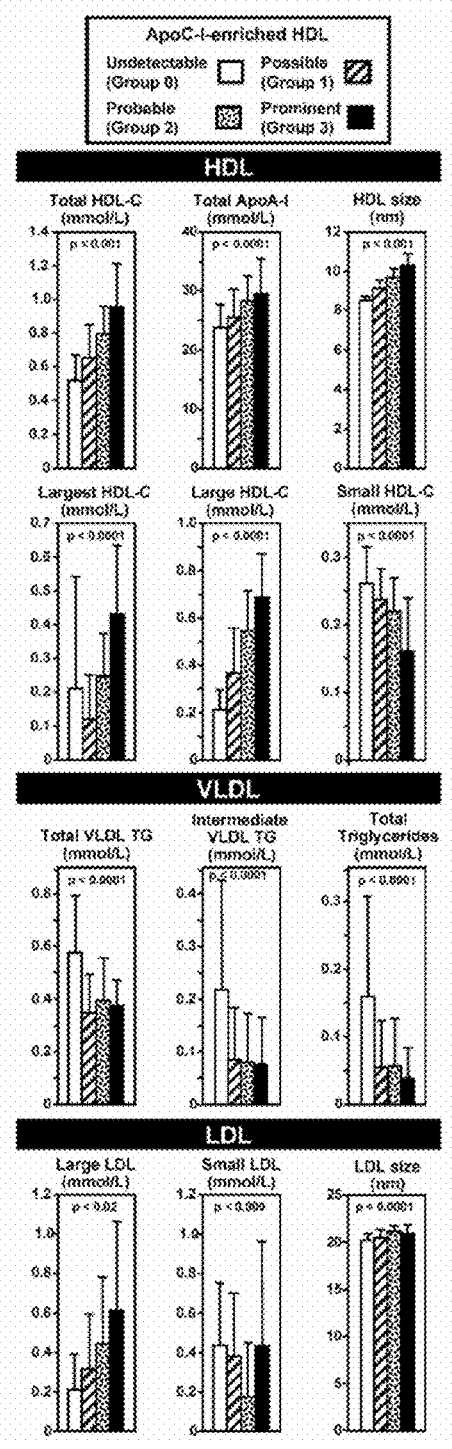
FIG. 14 depicts measured mean (1 SD) plasma levels of lipids, lipoprotein cholesterols, apolipoproteins, lipoprotein subclasses, and lipoprotein sizes were determined by nuclear magnetic resonance (NMR) spectroscopy (Otvos, J D. (2000) In: Rifai N. et al., Eds. Handbook of Lipoprotein Testing. Washington, D.C.:AACC Press, 609-623) in cord blood from group 0, 1, 2 and 3 infants. The p value given for each variable was corrected for the influence of gestational age by linear regression.

The levels of the lipid-related variables were determined in the four groups of infants (FIG. 14). Because of the influence of gestational age on the apoB- and apoA-I-containing lipoproteins in this population Kwiterovich Jr P O. et al. (In press, 2004) Ethn. Dis.), the p values were determined using data non-adjusted and adjusted for gestational age. Before age adjustment, all the variables except apoB and small VLDL were significantly different. After age adjustment, the only LDL variables that remained significantly higher in group 3 were L3, L1 and LDL size (FIG. 14). In contrast, all the HDL and VLDL related variables remained significantly different after correction for gestational age (FIG. 14). Large HDL levels were higher while small HDL and the VLDL related variables were lower in group 3. We also examined age-corrected means, which were very similar to the measured mean levels shown in FIG. 14 for the HDL- and VLDL-related variables. Differences between large LDL and large HDL in groups 0, 1, 2, and 3 (FIG. 14) were independent of triglycerides and VLDL.

Despite the fact that the gestational ages were very similar in groups 0, 1 and 2, there were also impressive dose-response relationships for the levels of all six of the HDL-related variables from class 0 through class 1, 2 and 3 infants (FIG. 14). These analyses further support the conclusion that the differences for the HDL subclasses shown in FIG. 14 were independent of age.

Example 14

Distribution of Gestational Age in Infants in Groups 0, 1, 2 and 3

Figure 15:
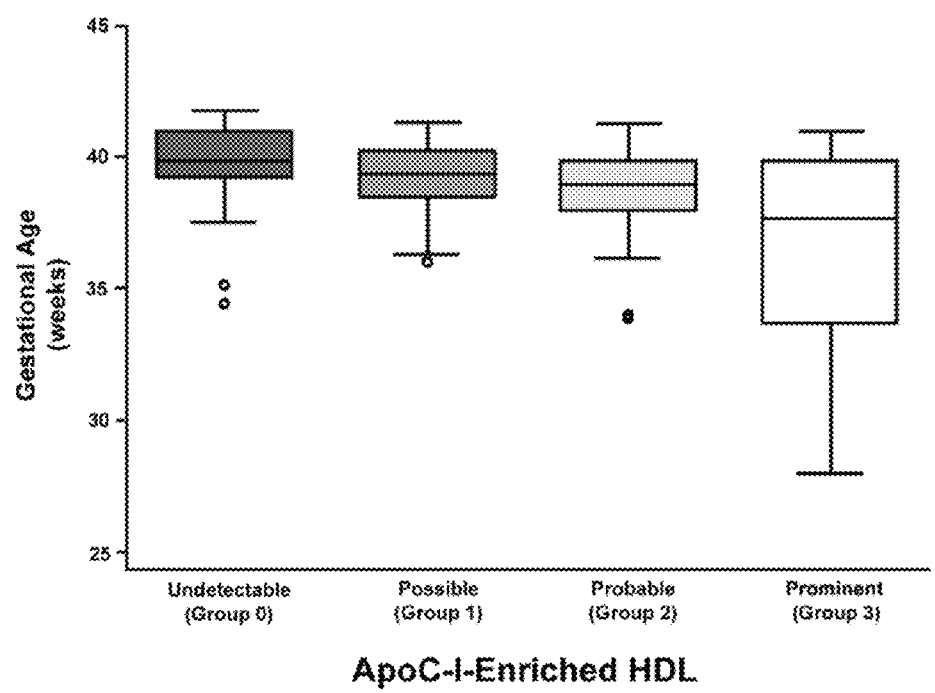
FIG. 15 depicts gestational age in group 0, 1, 2, and 3 infants. The median and $25^{th}$ and $75^{th}$ percentiles (box) and $5^{th}$ and $95^{th}$ percentiles (whiskers) for gestational age are shown. The circles represent outliers.

The gestational ages (mean (1 SD), in weeks) in groups, 0, 1, 2 and 3 were: 39.7 (1.75); 39.3 (1.28); 38.8 (1.68); and 36.2 (4.16), respectively, and differed significantly (p<0.0001). The mean gestational age in group 3 infants was not only younger, but had a distribution that was clearly broader than those in groups 0, 1, and 2 (FIG. 15).

The birth weights (grams) in group 0, 1, 2 and 3 infants were (mean (ISD)): 3268.6 (631.9); 3412.2 (548.3); 3240.6 (609.2); and 2683.7 (783.3), respectively, and differed significantly (p<0.0001), being particularly low in group 3. After correcting for gestational age, the birth weights were no longer significant (p=0.15). There were no significant differences in the numbers of male and female (p=0.38), white and black (p=0.88), or SGA and AGA (p=0.34) infants between the four groups.

Figure 16:
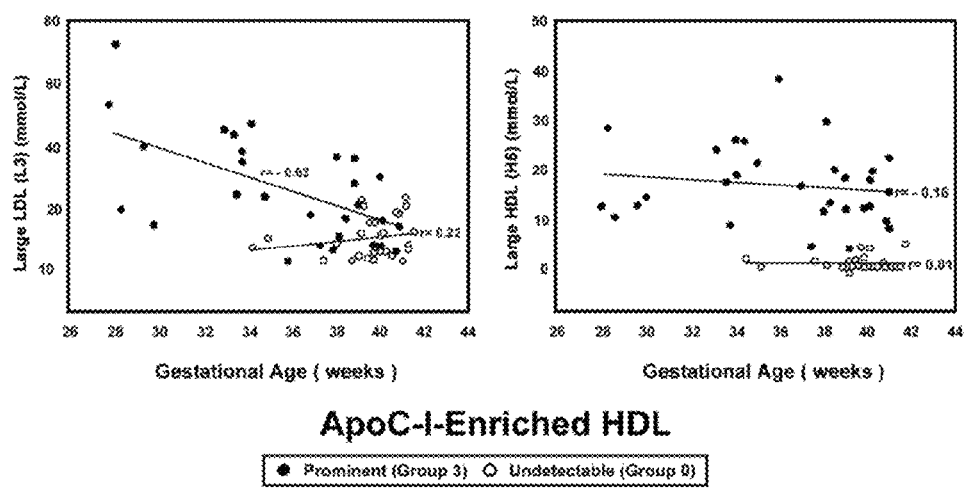
FIG. 16 depicts plots of gestational age versus large (L3) LDL cholesterol (left) and largest (H5) HDL cholesterol (right) in group 3 (solid circles) and group 0 (open circles) infants. Regression lines are depicted for each group.

We next plotted the levels of large LDL (L3) and largest HDL (H5) against gestational age for the group 3 and group 0 infants (FIG. 16). Group 3 infants had higher values of L3 than group 0 infants, but these L3 levels decreased dramatically with increasing gestational age. In distinct contrast, the higher H5 levels in group 3 did not fall with gestational age, indicating strongly that the elevated amount of ApoCI-enriched HDL in group 3 persisted and was not simply a consequence of younger gestational age (FIG. 16).

Example 15

ApoCI and CETP Activity

ApoCI levels in adults are associated with decreased CETP activity and larger HDL particles (Jong M C. et al. (1999) Arterioscler Thromb Vasc Biol 19:472-484; Gautier T. et al. (2000) J Biol Chem. 275:37504-37509). We examined if higher ApoCI levels in cord blood inhibited CETP activity, accounting for the different amounts of the large HDL particles. In a subset of 40 infants (group 0 N=17; group 3 N=13; and groups 1 and 2, N=10), there was no relationship between CETP activity (μM/ml) (range 0.0620 to 1.398) and ApoCI levels (umol/L) (range 2.3 to 20.7), r=0.087, NS. In a larger group (N=123) of infants, there was no significant difference (p=0.149) in CETP activity between the four groups.

TABLE 2

Apolipoprotein content of plasma, heparin-manganese supernatant, and heparin-manganese precipitate in infants with prominent (Group 3) or undetectable (Group 0) ApoCI-enriched HDL.

| Apolipoproteins | | Group 3 Infants (N = 5) | Group 0 Infants (N = 5) | P |
|---|---|---|---|---|
| ApoB | Plasma | 27.4(12.2)* | 21.4(2.3) | 0.53 |
| | Heparin-Mn$^{+2}$ | | | |
| | Supernatant | 0 | 0 | 1.0 |
| | Precipitate | 23.1(12.6) | 16.3(1.5) | 0.46 |
| ApoCI | Plasma | 8.7(1.9) | 4.8(2.4) | 0.08 |
| | Heparin-Mn$^{+2}$ | | | |
| | Supernatant | 6.9(3.1) | 3.3(1.8) | 0.03 |
| | Precipitate | 0 | 0 | 1.0 |
| ApoCIII | Plasma | 5.4(1.1) | 4.3(1.1) | 0.25 |
| | Heparin-Mn$^{+2}$ | | | |
| | Supernatant | 4.7(0.9) | 3.1(0.6) | 0.01 |
| | Precipitate | 0.6(0.3) | 1.3(0.6) | 0.05 |
| ApoA-I | Plasma | 119.7(38.8) | 99.6(17.1) | 0.46 |
| | Heparin-Mn$^{+2}$ | | | |
| | Supernatant | 101.6(30.7) | 83.0(11.6) | 0.12 |
| | Precipitate | 4.9(0.9) | 3.1(0.8) | 0.01 |
| ApoA-II | Plasma | 21.4(2.1) | 21.1(1.6) | 0.60 |

TABLE 2-continued

Apolipoprotein content of plasma, heparin-manganese supernatant, and heparin-manganese precipitate in infants with prominent (Group 3) or undetectable (Group 0) ApoCI-enriched HDL.

| Apolipoproteins | Group 3 Infants (N = 5) | Group 0 Infants (N = 5) | P |
|---|---|---|---|
| Heparin-Mn$^{+2}$ | | | |
| Supernatant | 19.8(2.2) | 19.8(0.8) | 0.46 |
| Precipitate | 0.9(0.2) | 0.9(0.2) | 0.91 |

*Mean(SD)

The invention has been described in detail with reference to preferred embodiments thereof. However, it will be appreciated that those skilled in the art, upon consideration of this disclosure, may make modification and improvements within the spirit and scope of the invention as set forth in the following claims.

What is claimed is:

1. A method for identifying a subject at risk of developing atherosclerosis-associated plaque rupture or myocardial infarction comprising:
   a) obtaining a blood, serum, or plasma sample from the subject;
   b) measuring the level of Apolipoprotein A-I:Apolipoprotein A-II lipoprotein particles (Lp-A-I:II) containing Apolipoprotein C-1 (ApoCI) in the sample, thereby measuring the level of ApoCI-enriched HDL in the sample;
   c) comparing the level of ApoCI-enriched HDL in the sample to the level of ApoCI-enriched HDL from a control; and
   d) identifying the subject as at risk of developing atherosclerosis-associated plaque rupture or myocardial infarction when the ApoCI-enriched HDL level is increased in the sample as compared to the control.

2. The method of claim 1, wherein the sample comprises elevated levels of large HDL.

3. The method of claim 1, wherein the subject is female.

4. The method of claim 1, wherein the subject has been previously diagnosed with atherosclerosis.

5. The method of claim 1, further comprising removing Apolipoprotein B (ApoB) from the sample prior to step b).

* * * * *